(12) United States Patent
Kitada et al.

(10) Patent No.: US 7,635,751 B2
(45) Date of Patent: Dec. 22, 2009

(54) PEPTIDES HAVING LIGAND ACTIVITIES ON APJ THAT IS AN ORPHAN G PROTEIN-COUPLED RECEPTOR, AND USE THEREOF

(75) Inventors: Chieko Kitada, Sakai (JP); Naoki Nishizawa, Amagasaki (JP); Shuji Hinuma, Tsukuba (JP); Masaki Hosoya, Tsuchiura (JP)

(73) Assignee: Takada Pharmaceutical Company Limited, Osaka (JP)

( * ) Notice: Subject to any disclaimer, the term of this patent is extended or adjusted under 35 U.S.C. 154(b) by 1119 days.

(21) Appl. No.: 10/239,321

(22) PCT Filed: Mar. 22, 2001

(86) PCT No.: PCT/JP01/02278

§ 371 (c)(1),
(2), (4) Date: Sep. 19, 2002

(87) PCT Pub. No.: WO01/70769

PCT Pub. Date: Sep. 27, 2001

(65) Prior Publication Data

US 2004/0116336 A1    Jun. 17, 2004

(30) Foreign Application Priority Data

Mar. 23, 2000    (JP) ............................. 2000-087114
Sep. 19, 2000    (JP) ............................. 2000-288891

(51) Int. Cl.
C07K 7/06    (2006.01)
C07K 7/08    (2006.01)
A61K 38/08    (2006.01)
A61K 38/10    (2006.01)

(52) U.S. Cl. ............................ 530/327; 514/2; 514/14; 514/15; 530/300; 530/328

(58) Field of Classification Search .................. None
See application file for complete search history.

(56) References Cited

U.S. PATENT DOCUMENTS 6,475,718 B2 * 11/2002 Doms et al. ................... 435/5

6,492,324 B1 * 12/2002 Hinuma et al. ................. 514/2

FOREIGN PATENT DOCUMENTS

| WO | WO 94/12635 | * | 6/1994 |
| WO | WO 99/33976 | * | 7/1999 |
| WO | WO 00/18793 | * | 4/2000 |

OTHER PUBLICATIONS

Nishizawa et al. High Potency Analogs of Apelin, a Ligand of Orphan GPCR APJ. Peptide Science 2000. 37th, pp. 151-154.*
Tatemoto et al. The novel peptide apelin lowers blood pressure . . . Regulatory Peptides. 2001, vol. 99, pp. 87-92.*
Cayabyab, et al. "Apelin, the Natural Ligand of the Orphan Seven-Transmembrane Receptor APJ, Inhibits Human Immunodeficiency Virus Type I Entry". Journal of Virology 74(24):11972-11976 (Dec. 2000).*
Zou, et al. "Apelin peptides block the entry of human immunodeficiency virus (HIV)". FEBS Lett 473:15-18 (2000).*
Tatemoto, et al. "Isolation and Characterization of a Novel Endogenous Peptide Ligand for the Human APJ Receptor". BBRC 251:471-476 (1998).*
O'Dowd, et al. "A human gene that shows identity with the gene encoding the angiotensin receptor is located on chromosome 11". GENE 136:355-360 (1993).*

* cited by examiner

Primary Examiner—Jeffrey E Russel
(74) Attorney, Agent, or Firm—David G Conlin; Gregory B Butler, Esq.; Edwards Angell Palmer & Dodge LLP

(57) ABSTRACT

The present invention relates to novel peptide derivatives, which are recognized as ligands to G-coupled protein receptor proteins.

The peptide of the present invention can be used in (1) development of a receptor binding assay system using the expression system of the recombinant receptor protein and screening of candidates for pharmaceutical compounds, and (2) development of pharmaceutical preparations such as a neutral nerve function regulator, a circulatory function regulator, a cardiac function regulator, an immune function regulator, a digestive organ function regulator, a metabolic function regulator, a generative organ regulator or the like.

6 Claims, No Drawings ically modifying a naturally

SEQUENCE LISTING

```
<160> NUMBER OF SEQ ID NOS: 72

<210> SEQ ID NO 1
<211> LENGTH: 15
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (15)..(15)
<223> OTHER INFORMATION: Xaa means Phe(Cl)

<400> SEQUENCE: 1

Arg Arg Gln Arg Pro Arg Leu Ser Ala Arg Gly Pro Met Pro Xaa
 1               5                  10                  15

<210> SEQ ID NO 2
<211> LENGTH: 15
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (13)..(13)
<223> OTHER INFORMATION: Xaa on the 13th position means Cha
<220> FEATURE:
<221> NAME/KEY: MISC_FEATURE
<222> LOCATION: (15)..(15)
<223> OTHER INFORMATION: Xaa on the 15th position means Phe(Cl)

<400> SEQUENCE: 2

Arg Arg Gln Arg Pro Arg Leu Ser His Lys Gly Pro Xaa Pro Xaa
 1               5                  10                  15

<210> SEQ ID NO 3
<211> LENGTH: 12
<212> TYPE: PRT
<213> ORGANISM: Artificial
```

```
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means Phe(Cl)

<400> SEQUENCE: 3

Arg Pro Arg Leu Ser Ala Arg Gly Pro Met Pro Xaa
 1               5                  10

<210> SEQ ID NO 4
<211> LENGTH: 11
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha,
<220> FEATURE:
<221> NAME/KEY: MISC_FEATURE
<222> LOCATION: (11)..(11)
<223> OTHER INFORMATION: Xaa on the 11th position means Phe(Cl).

<400> SEQUENCE: 4

Arg Pro Arg Leu Ser Ala Arg Gly Pro Xaa Xaa
 1               5                  10

<210> SEQ ID NO 5
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha.
<220> FEATURE:
<221> NAME/KEY: MISC_FEATURE
<222> LOCATION: (12)..(12)
<223> OTHER INFORMATION: Xaa on the 12th position means Phe(Cl).

<400> SEQUENCE: 5

Arg Pro Arg Leu Ser Ala Arg Gly Pro Xaa Pro Xaa
 1               5                  10

<210> SEQ ID NO 6
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (13)..(13)
<223> OTHER INFORMATION: Xaa means Cha.

<400> SEQUENCE: 6

Arg Arg Gln Arg Pro Arg Leu Ser Ala Arg Gly Pro Xaa
 1               5                  10

<210> SEQ ID NO 7
<211> LENGTH: 12
<212> TYPE: PRT
<213> ORGANISM: Artificial
<220> FEATURE:
<223> OTHER INFORMATION: peptide derivative
<220> FEATURE:
```

```
<221> NAME/KEY: MISC_FEATURE
<222> LOCATION: (10)..(10)
<223> OTHER INFORMATION: Xaa on the 10th position means Cha.
<220> FEATURE:
<221> NAME/KEY: MISC_FEATURE
<222> LOCATION: (12)..(12)
<223> OTHER INFORMATION: Xaa on the 12th position means Phe(Cl).

<400> SEQUENCE: 7

Arg Pro Arg Leu Ser His Lys Gly Pro Xaa Pro Xaa
 1               5                  10

<210> SEQ ID NO 8
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means Phe(Cl).

<400> SEQUENCE: 8

Arg Pro Arg Leu Ser His Lys Gly Pro Met Pro Xaa
 1               5                  10

<210> SEQ ID NO 9
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa on the 1st position means pGlu.
<220> FEATURE:
<221> NAME/KEY: MISC_FEATURE
<222> LOCATION: (11)..(11)
<223> OTHER INFORMATION: Xaa on the 11th position means Cha.

<400> SEQUENCE: 9

Xaa Arg Pro Arg Leu Ser His Lys Gly Pro Xaa Pro Phe
 1               5                  10

<210> SEQ ID NO 10
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa on the 1st position means pGlu.
<220> FEATURE:
<221> NAME/KEY: MISC_FEATURE
<222> LOCATION: (13)..(13)
<223> OTHER INFORMATION: Xaa on the 13th position means Phe(Cl).

<400> SEQUENCE: 10

Xaa Arg Pro Arg Leu Ser His Lys Gly Pro Met Pro Xaa
 1               5                  10

<210> SEQ ID NO 11
<211> LENGTH: 12
<212> TYPE: PRT
<213> ORGANISM: Artificial
<220> FEATURE:
<223> OTHER INFORMATION: peptide derivative
```

```
<220> FEATURE:
<221> NAME/KEY: MISC_FEATURE
<222> LOCATION: (10)..(10)
<223> OTHER INFORMATION: Xaa means Cha.

<400> SEQUENCE: 11

Arg Pro Arg Leu Ser Ala Arg Gly Pro Xaa Pro Phe
 1               5                  10

<210> SEQ ID NO 12
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha.
<220> FEATURE:
<221> NAME/KEY: MISC_FEATURE
<222> LOCATION: (12)..(12)
<223> OTHER INFORMATION: Xaa on the 12th position means Phe(Cl).

<400> SEQUENCE: 12

Arg Pro Arg Leu Phe Ala Arg Gly Pro Xaa Pro Xaa
 1               5                  10

<210> SEQ ID NO 13
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha.
<220> FEATURE:
<221> NAME/KEY: MISC_FEATURE
<222> LOCATION: (12)..(12)
<223> OTHER INFORMATION: Xaa on the 12th position means Phe(Cl).

<400> SEQUENCE: 13

Arg Pro Arg Leu Phe His Lys Gly Pro Xaa Pro Xaa
 1               5                  10

<210> SEQ ID NO 14
<211> LENGTH: 15
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (13)..(13)
<223> OTHER INFORMATION: Xaa means Nle.

<400> SEQUENCE: 14

Arg Arg Gln Arg Pro Arg Leu Ser His Lys Gly Pro Xaa Pro Tyr
 1               5                  10                  15

<210> SEQ ID NO 15
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
```

<223> OTHER INFORMATION: Xaa means Cha.

<400> SEQUENCE: 15

Arg Pro Arg Leu Phe His Lys Gly Pro Xaa Pro Phe
1               5                   10

<210> SEQ ID NO 16
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means Phe(Cl).

<400> SEQUENCE: 16

Arg Pro Arg Leu Phe His Lys Gly Pro Met Pro Xaa
1               5                   10

<210> SEQ ID NO 17
<211> LENGTH: 36
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (34)..(34)
<223> OTHER INFORMATION: Xaa means Nle.

<400> SEQUENCE: 17

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
                20                  25                  30

Pro Xaa Pro Tyr
        35

<210> SEQ ID NO 18
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa on the 1st position means pGlu.
<220> FEATURE:
<221> NAME/KEY: MISC_FEATURE
<222> LOCATION: (11)..(11)
<223> OTHER INFORMATION: Xaa on the 11th position means Nle.

<400> SEQUENCE: 18

Xaa Arg Pro Arg Leu Ser His Lys Gly Pro Xaa Pro Tyr
1               5                   10

<210> SEQ ID NO 19
<211> LENGTH: 380
<212> TYPE: PRT
<213> ORGANISM: Artificial
<220> FEATURE:
<223> OTHER INFORMATION: protein

<400> SEQUENCE: 19

Met Glu Glu Gly Gly Asp Phe Asp Asn Tyr Tyr Gly Ala Asp Asn Gln

|    |     |     |     |     |     |     |     |     |     |     |     |     |
|----|-----|-----|-----|-----|-----|-----|-----|-----|-----|-----|-----|-----|
| 1  |     |     |     | 5   |     |     |     |     | 10  |     |     |     | 15 |

Ser Glu Cys Glu Tyr Thr Asp Trp Lys Ser Gly Ala Leu Ile Pro
                 20                  25                  30

Ala Ile Tyr Met Leu Val Phe Leu Leu Gly Thr Thr Gly Asn Gly Leu
             35                  40                  45

Val Leu Trp Thr Val Phe Arg Ser Ser Arg Glu Lys Arg Arg Ser Ala
         50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                 85                  90                  95

Phe Gly Thr Phe Phe Cys Lys Leu Ser Ser Tyr Leu Ile Phe Val Asn
                100                 105                 110

Met Tyr Ala Ser Val Phe Cys Leu Thr Gly Leu Ser Phe Asp Arg Tyr
                115                 120                 125

Leu Ala Ile Val Arg Pro Val Ala Asn Ala Arg Leu Arg Leu Arg Val
            130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
                180                 185                 190

Ser Glu Trp Ala Trp Glu Val Gly Leu Gly Val Ser Ser Thr Thr Val
            195                 200                 205

Gly Phe Val Val Pro Phe Thr Ile Met Leu Thr Cys Tyr Phe Phe Ile
            210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
                260                 265                 270

Leu Gly Ser Leu Leu His Trp Pro Cys Asp Phe Asp Leu Phe Leu Met
            275                 280                 285

Asn Ile Phe Pro Tyr Cys Thr Cys Ile Ser Tyr Val Asn Ser Cys Leu
                290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
                340                 345                 350

Gly Pro Gly Pro Asn Met Gly Lys Gly Gly Glu Gln Met His Glu Lys
            355                 360                 365

Ser Ile Pro Tyr Ser Gln Glu Thr Leu Val Val Asp
            370                 375                 380

<210> SEQ ID NO 20
<211> LENGTH: 1140
<212> TYPE: DNA
<213> ORGANISM: Artificial
<220> FEATURE:
<223> OTHER INFORMATION: encoding nucleic acid

```
<400> SEQUENCE: 20
atggaggaag gtggtgattt tgacaactac tatggggcag acaaccagtc tgagtgtgag      60
tacacagact ggaaatcctc gggggccctc atccctgcca tctacatgtt ggtcttcctc     120
ctgggcacca cgggaaacgg tctggtgctc tggaccgtgt tcggagcag ccgggagaag      180 aggcgctcag ctgatatctt cattgctagc ctggcggtgg ctgacctgac cttcgtggtg     240
acgctgcccc tgtgggctac ctacacgtac cgggactatg actggccctt tgggaccttc     300
ttctgcaagc tcagcagcta cctcatcttc gtcaacatgt acgccagcgt cttctgcctc     360
accggcctca gcttcgaccg ctacctggcc atcgtgaggc agtggccaa tgctcggctg      420 aggctgcggg tcagcggggc cgtggccacg gcagttcttt gggtgctggc cgccctcctg     480
gccatgcctg tcatggtgtt acgcaccacc ggggacttgg agaacaccac taaggtgcag     540
tgctacatgg actactccat ggtggccact gtgagctcag agtgggcctg ggaggtgggc     600 cttgggtct cgtccaccac cgtgggcttt gtggtgccct tcaccatcat gctgacctgt     660
tacttcttca tcgcccaaac catcgctggc cacttccgca aggaacgcat cgagggcctg     720
cggaagcggc gccggctgct cagcatcatc gtggtgctgg tggtgacctt tgccctgtgc     780
tggatgccct accacctggt gaagacgctg tacatgctgg cagcctgct gcactggccc     840 tgtgactttg acctcttcct catgaacatc ttccccctact gcacctgcat cagctacgtc     900
aacagctgcc tcaaccccct cctctatgcc tttttcgacc ccgcttccg ccaggcctgc     960 acctccatgc tctgctgtgg ccagagcagg tgcgcaggca cctcccacag cagcagtggg    1020
gagaagtcag ccagctactc ttcggggcac agccaggggc ccggccccaa catgggcaag    1080
ggtggagaac agatgcacga gaaatccatc ccctacagcc aggagaccct tgtggttgac    1140

<210> SEQ ID NO 21
<211> LENGTH: 15
<212> TYPE: PRT
<213> ORGANISM: Artificial
<220> FEATURE:
<223> OTHER INFORMATION: peptide derivative

<400> SEQUENCE: 21

Arg Arg Gln Arg Pro Arg Leu Ser Ala Arg Gly Pro Met Pro Phe
1               5                   10                  15

<210> SEQ ID NO 22
<211> LENGTH: 13
<212> TYPE: PRT
<213> ORGANISM: Artificial
<220> FEATURE:
<223> OTHER INFORMATION: peptide derivative

<400> SEQUENCE: 22

Arg Arg Gln Arg Pro Arg Leu Ser Ala Arg Gly Pro Met
1               5                   10          13

<210> SEQ ID NO 23
<211> LENGTH: 12
<212> TYPE: PRT
<213> ORGANISM: Artificial
<220> FEATURE:
<223> OTHER INFORMATION: peptide derivative

<400> SEQUENCE: 23

Arg Arg Gln Arg Pro Arg Leu Ser Ala Arg Gly Pro
1               5                   10      12
```

```
<210> SEQ ID NO 24
<211> LENGTH: 13
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (13)..(13)
<223> OTHER INFORMATION: Xaa means Met(O)

<400> SEQUENCE: 24

Arg Arg Gln Arg Pro Arg Leu Ser His Lys Gly Pro Xaa
1               5                   10          13

<210> SEQ ID NO 25
<211> LENGTH: 15
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (3)..(3)
<223> OTHER INFORMATION: Xaa means Lys(Arg-Arg)

<400> SEQUENCE: 25

Arg Arg Xaa Arg Pro Arg Leu Ser His Lys Gly Pro Met Pro Phe
1               5                   10                  15

<210> SEQ ID NO 26
<211> LENGTH: 15
<212> TYPE: PRT
<213> ORGANISM: Artificial
<220> FEATURE:
<223> OTHER INFORMATION: peptide derivative

<400> SEQUENCE: 26

Arg Arg Arg Arg Pro Arg Leu Ser His Lys Gly Pro Met Pro Phe
1               5                   10                  15

<210> SEQ ID NO 27
<211> LENGTH: 15
<212> TYPE: PRT
<213> ORGANISM: Artificial
<220> FEATURE:
<223> OTHER INFORMATION: peptide derivative

<400> SEQUENCE: 27

Arg Arg Lys Arg Pro Arg Leu Ser His Lys Gly Pro Met Pro Phe
1               5                   10                  15

<210> SEQ ID NO 28
<211> LENGTH: 12
<212> TYPE: PRT
<213> ORGANISM: Artificial
<220> FEATURE:
<223> OTHER INFORMATION: peptide derivative

<400> SEQUENCE: 28

Arg Pro Arg Leu Ser Ala Arg Gly Pro Met Pro Phe
1               5                   10      12

<210> SEQ ID NO 29
<211> LENGTH: 15
<212> TYPE: PRT
<213> ORGANISM: Artificial
<220> FEATURE:
```

```
<223> OTHER INFORMATION: peptide derivative

<400> SEQUENCE: 29

Arg Arg Ala Arg Pro Arg Leu Ser His Lys Gly Pro Met Pro Phe
1               5                   10                  15

<210> SEQ ID NO 30
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa means pGlu

<400> SEQUENCE: 30

Xaa Arg Pro Arg Leu Ser Ala Arg Gly Pro Met Pro Phe
1               5                   10          13

<210> SEQ ID NO 31
<211> LENGTH: 10
<212> TYPE: PRT
<213> ORGANISM: Artificial
<220> FEATURE:
<223> OTHER INFORMATION: peptide derivative

<400> SEQUENCE: 31

Arg Pro Arg Leu Ser Ala Arg Gly Pro Met
1               5                   10

<210> SEQ ID NO 32
<211> LENGTH: 11
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (11)..(11)
<223> OTHER INFORMATION: Xaa means Phe(Cl)

<400> SEQUENCE: 32

Arg Pro Arg Leu Ser His Lys Gly Pro Met Xaa
1               5                   10  11

<210> SEQ ID NO 33
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa means pGlu

<400> SEQUENCE: 33

Xaa Arg Pro Arg Leu Ser Ala Lys Gly Pro Met Pro Phe
1               5                   10          13

<210> SEQ ID NO 34
<211> LENGTH: 13
<212> TYPE: PRT
<213> ORGANISM: Artificial
<220> FEATURE:
<223> OTHER INFORMATION: peptide derivative
<220> FEATURE:
```

```
<221> NAME/KEY: MISC_FEATURE
<222> LOCATION: (1)..(1)
<223> OTHER INFORMATION: Xaa means pGlu

<400> SEQUENCE: 34

Xaa Arg Pro Arg Leu Ser Arg Lys Gly Pro Met Pro Phe
1               5                   10              13

<210> SEQ ID NO 35
<211> LENGTH: 12
<212> TYPE: PRT
<213> ORGANISM: Artificial
<220> FEATURE:
<223> OTHER INFORMATION: peptide derivative

<400> SEQUENCE: 35

Arg Pro Arg Leu Phe Ala Arg Gly Pro Met Pro Phe
1               5                   10      12

<210> SEQ ID NO 36
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means Nal(2)

<400> SEQUENCE: 36

Arg Pro Arg Leu Ser His Lys Gly Pro Met Pro Xaa
1               5                   10      12

<210> SEQ ID NO 37
<211> LENGTH: 15
<212> TYPE: PRT
<213> ORGANISM: Artificial
<220> FEATURE:
<223> OTHER INFORMATION: peptide derivative

<400> SEQUENCE: 37

Arg Arg Phe Arg Pro Arg Leu Ser His Lys Gly Pro Met Pro Phe
1               5                   10                  15

<210> SEQ ID NO 38
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa means pGlu

<400> SEQUENCE: 38

Xaa Arg Pro Arg Leu Ser His Arg Gly Pro Met Pro Phe
1               5                   10              13

<210> SEQ ID NO 39
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
```

```
<223> OTHER INFORMATION: Xaa on the 1st position means pGlu.
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 39

Xaa Arg Pro Arg Leu Ser His Lys Gly Pro Met Xaa
1               5                   10  12

<210> SEQ ID NO 40
<211> LENGTH: 11
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (11)..(11)
<223> OTHER INFORMATION: Xaa means Cha

<400> SEQUENCE: 40

Arg Pro Arg Leu Ser His Lys Gly Pro Met Xaa
1               5                   10  11

<210> SEQ ID NO 41
<211> LENGTH: 11
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(11)
<223> OTHER INFORMATION: Xaa on the 10th position means Cha, Xaa on the
      11th position means Phe(Cl)
<400> SEQUENCE: 41

Arg Pro Arg Leu Phe His Lys Gly Pro Xaa Xaa
1               5                   10  11

<210> SEQ ID NO 42
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa means pGlu

<400> SEQUENCE: 42

Xaa Arg Pro Arg Leu Ser Leu Lys Gly Pro Met Pro Phe
1               5                   10          13

<210> SEQ ID NO 43
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa on the 1st position means pGlu.
<220> FEATURE:
<221> NAME/KEY: MISC_FEATURE
<222> LOCATION: (13)..(13)
<223> OTHER INFORMATION: Xaa on the 13th position means Nal(2)

<400> SEQUENCE: 43
```

```
Xaa Arg Pro Arg Leu Ser His Lys Gly Pro Met Pro Xaa
1               5                   10          13
```

<210> SEQ ID NO 44
<211> LENGTH: 11
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (11)..(11)
<223> OTHER INFORMATION: Xaa means Nal(2)

<400> SEQUENCE: 44

```
Arg Pro Arg Leu Ser His Lys Gly Pro Met Xaa
1               5                   10  11
```

<210> SEQ ID NO 45
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa means pGlu

<400> SEQUENCE: 45

```
Xaa Arg Pro Arg Leu Ser Arg Arg Gly Pro Met Pro Phe
1               5                   10          13
```

<210> SEQ ID NO 46
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa means pGlu

<400> SEQUENCE: 46

```
Xaa Arg Pro Arg Leu Phe Arg Arg Gly Pro Met Pro Phe
1               5                   10          13
```

<210> SEQ ID NO 47
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa means pGlu

<400> SEQUENCE: 47

```
Xaa Arg Pro Arg Leu Ser Phe Lys Gly Pro Met Pro Phe
1               5                   10          13
```

<210> SEQ ID NO 48
<211> LENGTH: 13
<212> TYPE: PRT
<213> ORGANISM: Artificial
<220> FEATURE:
<223> OTHER INFORMATION: peptide derivative

```
<220> FEATURE:
<221> NAME/KEY: MISC_FEATURE
<222> LOCATION: (1)..(1)
<223> OTHER INFORMATION: Xaa means pGlu

<400> SEQUENCE: 48

Xaa Arg Pro Arg Leu Phe His Lys Gly Pro Met Pro Phe
1               5                   10          13

<210> SEQ ID NO 49
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa on the 1st position means pGlu
<220> FEATURE:
<221> NAME/KEY: MISC_FEATURE
<222> LOCATION: (12)..(12)
<223> OTHER INFORMATION: Xaa on the 12th position means Cha

<400> SEQUENCE: 49

Xaa Arg Pro Arg Leu Ser His Lys Gly Pro Met Xaa
1               5                   10      12

<210> SEQ ID NO 50
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa on the 1st position means pGlu
<220> FEATURE:
<221> NAME/KEY: MISC_FEATURE
<222> LOCATION: (12)..(12)
<223> OTHER INFORMATION: Xaa on the 12th position means Nal(2)

<400> SEQUENCE: 50

Xaa Arg Pro Arg Leu Ser His Lys Gly Pro Met Xaa
1               5                   10      12

<210> SEQ ID NO 51
<211> LENGTH: 11
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION:

<400> SEQUENCE: 51

Arg Pro Arg Leu Phe Ala Arg Gly Pro Met Phe
1               5                   10  11

<210> SEQ ID NO 52
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
```

```
<223> OTHER INFORMATION: Xaa means pGlu

<400> SEQUENCE: 52

Xaa Arg Pro Arg Leu Ser His Phe Gly Pro Met Pro Phe
1               5                   10              13

<210> SEQ ID NO 53
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means Cha

<400> SEQUENCE: 53

Arg Pro Arg Leu Ser His Lys Gly Pro Met Pro Xaa
1               5                   10      12

<210> SEQ ID NO 54
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: Xaa means pGlu

<400> SEQUENCE: 54

Xaa Arg Pro Arg Leu Ser His Leu Gly Pro Met Pro Phe
1               5                   10              13

<210> SEQ ID NO 55
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means NMe2

<400> SEQUENCE: 55

Arg Arg Gln Arg Pro Arg Leu Ser Ala Arg Gly Xaa
1               5                   10      12

<210> SEQ ID NO 56
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means Mor

<400> SEQUENCE: 56

Arg Arg Gln Arg Pro Arg Leu Ser Ala Arg Gly Xaa
1               5                   10      12

<210> SEQ ID NO 57
<211> LENGTH: 12
<212> TYPE: PRT
```

<213> ORGANISM: Artificial
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means Phe(Cl)

<400> SEQUENCE: 57

Arg Pro Arg Leu Ser Ala Arg Gly Pro Ala Pro Xaa
1               5                   10      12

<210> SEQ ID NO 58
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (12)..(12)
<223> OTHER INFORMATION: Xaa means Phe(Cl)

<400> SEQUENCE: 58

Arg Pro Arg Leu Ser Ala Arg Gly Gly Met Pro Xaa
1               5                   10      12

<210> SEQ ID NO 59
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (09)..(09)
<223> OTHER INFORMATION: Xaa on the 9th position means N-MeAla
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 59

Arg Pro Arg Leu Ser Ala Arg Gly Xaa Met Pro Xaa
1               5                   10      12

<210> SEQ ID NO 60
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 60

Arg Pro Arg Leu Ser His Ala Gly Pro Xaa Pro Xaa
1               5                   10      12

<210> SEQ ID NO 61
<211> LENGTH: 12
<212> TYPE: PRT
<213> ORGANISM: Artificial
<220> FEATURE:
<223> OTHER INFORMATION: peptide derivative

```
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 61

Arg Pro Arg Ala Ser His Lys Gly Pro Xaa Pro Xaa
1               5                   10      12

<210> SEQ ID NO 62
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 62

Arg Pro Ala Leu Ser His Lys Gly Pro Xaa Pro Xaa
1               5                   10      12

<210> SEQ ID NO 63
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Phe(Cl)-NH2

<400> SEQUENCE: 63

Arg Pro Ala Leu Ser His Lys Gly Pro Xaa Pro Xaa
1               5                   10      12

<210> SEQ ID NO 64
<211> LENGTH: 11
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (11)..(11)
<223> OTHER INFORMATION: Xaa on the 11th position means Pyn

<400> SEQUENCE: 64

Arg Pro Arg Leu Ser Ala Arg Gly Pro Xaa Xaa
1               5                   10  11

<210> SEQ ID NO 65
```

```
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Pyn

<400> SEQUENCE: 65

Arg Pro Arg Leu Ser Ala Arg Gly Pro Xaa Pro Xaa
1               5                   10      12

<210> SEQ ID NO 66
<211> LENGTH: 13
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (13)..(13)
<223> OTHER INFORMATION: Xaa on the 13th position means Cha

<400> SEQUENCE: 66

Arg Arg Gln Arg Pro Arg Leu Ser Ala Arg Gly Gly Xaa
1               5                   10          13

<210> SEQ ID NO 67
<211> LENGTH: 12
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (03)..(03)
<223> OTHER INFORMATION: Xaa on the 3rd position means Lys(Me)2

<400> SEQUENCE: 67

Arg Pro Xaa Leu Ser Ala Arg Gly Pro Met Pro Phe
1               5                   10      12

<210> SEQ ID NO 68
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (07)..(07)
<223> OTHER INFORMATION: Xaa on the 7th position means Lys(Me)2

<400> SEQUENCE: 68

Arg Pro Arg Leu Ser Ala Xaa Gly Pro Met Pro Phe
1               5                   10      12

<210> SEQ ID NO 69
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
```

```
<222> LOCATION: (06)..(06)
<223> OTHER INFORMATION: Xaa on the 6th position means Dap
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 69

Arg Pro Arg Leu Ser Xaa Arg Gly Pro Xaa Pro Xaa
1               5                   10      12

<210> SEQ ID NO 70
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (06)..(06)
<223> OTHER INFORMATION: Xaa on the 6th position means Dap(Ac)
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 70

Arg Pro Arg Leu Ser Xaa Arg Gly Pro Xaa Pro Xaa
1               5                   10      12

<210> SEQ ID NO 71
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (06)..(06)
<223> OTHER INFORMATION: Xaa on the 6th position means Dap(C6)
<220> FEATURE:
<221> NAME/KEY: MISC_FEATURE
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 71

Arg Pro Arg Leu Ser Xaa Arg Gly Pro Xaa Pro Xaa
1               5                   10      12

<210> SEQ ID NO 72
<211> LENGTH: 12
<212> TYPE: PRT
<213> ORGANISM: Artificial
<220> FEATURE:
<223> OTHER INFORMATION: peptide derivative
<220> FEATURE:
<221> NAME/KEY: MISC_FEATURE
<222> LOCATION: (06)..(06)
<223> OTHER INFORMATION: Xaa on the 6th position means Dap(Adi)
<220> FEATURE:
<221> NAME/KEY: MISC_FEATURE
```

```
<222> LOCATION: (10)..(10)
<223> OTHER INFORMATION: Xaa on the 10th position means Cha
<220> FEATURE:
<221> NAME/KEY: MISC_FEATURE
<222> LOCATION: (12)..(12)
<223> OTHER INFORMATION: Xaa on the 12th position means Phe(Cl)

<400> SEQUENCE: 72

Arg Pro Arg Leu Ser Xaa Arg Gly Pro Xaa Pro Xaa
1               5                   10      12
```

PEPTIDES HAVING LIGAND ACTIVITIES ON APJ THAT IS AN ORPHAN G PROTEIN-COUPLED RECEPTOR, AND USE THEREOF This application is the National Phase filing of International Patent Application No. PCT/JP01/02278, filed Mar. 22, 2001.

TECHNICAL FIELD

The present invention relates to a novel peptide having a ligand activity on APJ that is an orphan G protein-coupled receptor protein, use thereof, etc.

BACKGROUND ART

Many hormones and neurotransmitters regulate the biological function via specific receptors present on cell membranes. Many of these receptors are coupled with guanine nucleotide-binding protein (hereinafter sometimes simply referred to as G protein) and mediate the intracellular signal transduction via activation of G protein, and these receptor proteins possess the common structure containing seven transmembrane domains and are thus collectively referred to as G protein-coupled receptors or seven-transmembrane receptors (7TMR).

Regulation of functions important for the living body, such as maintenance of homeostasis in the living body, reproduction, development of individuals, metabolism, growth, and regulation in the nerve system, circulatory organ system, immune system, digestive organ system and metabolic system, is carried out through interaction of hormones or neurotransmitters with G protein-coupled receptors. For regulation of biological functions, receptor proteins are known to occur for various hormones and neurotransmitters and play an important role in regulating their functions, but there still remain many unrevealed features as to unknown agonists (hormones, neurotransmitters etc.) and presence of receptors therefor.

Utilizing homology of a partial structure of G protein-coupled receptor proteins to receptor amino acid sequences, a method of searching for DNA encoding a novel receptor protein has been carried out in recent years by use of polymerase chain reaction (abbreviated hereinafter into PCR), and a large number of orphan G protein-coupled receptor proteins whose ligands are not known have been cloned (Libert, F., et al. Science, 244, 569-572, 1989, Welch, S. K., et al., Biochem. Biophys. Res. Commun., 209, 606-613, 1995, Marchese, A., et al., Genomics, 23, 609-618, 1994, Marchese, A., Genomics, 29, 335-344, 1995). Further, novel G protein-coupled receptor proteins have been found one after another by random sequencing of genomic DNA or cDNA (Nomura, N., et al., DNA Research, 1, 27-35, 1994). The general means of determining ligands for these orphan G protein-coupled receptor proteins depended conventionally on mere estimation from homology in the primary structure of the G protein-coupled receptor protein. However, a large number of orphan G protein-coupled receptor proteins have low homology to known receptors, thus making it actually difficult to estimate their corresponding ligands on only the basis of homology in the primary structure except for receptor subtypes of known ligands. On the other hand, a large number of orphan G protein-coupled receptors have been found through gene analysis, and thus it is estimated that a large number of their corresponding unknown ligands are present, but there are few reports on actual identification of ligands for orphan G protein-coupled receptors.

Recently, there are reports wherein a novel opioid peptide was searched for by introducing cDNA encoding an orphan G protein-coupled receptor protein into an animal cell (Reinsheld, R. K. et al., Science, 270, 792-794, 1995, Menular, J.-C., et al., Nature, 377, 532-535, 1995). However, the ligand in this case had been estimated to belong to a family of opioid peptides from homology to known G protein-coupled receptors and distribution in tissues. There is a long history of research and development of substances acting on the living body via opioid receptors, and various antagonists and agonists have been developed. In such development, an agonist to this receptor is found from a group of artificially synthesized compounds and used as a probe to verify expression of the receptor in cells having receptor cDNA introduced therein, and an activating substance similar to the agonist is searched for in the intracellular information transmission system and purified to determine the structure of the ligand.

Further, there is also a report wherein cDNA encoding an orphan G protein-coupled receptor (GRL104) from a snail is introduced into CHO cells, and a novel physiologically active peptide has been identified by using, as an indicator, an increase in specific intracellular calcium levels in the cells expressing the receptor (Cox, K. J. A., et al., J. Neurosci., 17(4), 1197-1205, 1997), but this novel physiologically active peptide had high homology to known leucokinin, and GRL104 was also reactive with known leucokinin. Accordingly, there are few orphan G protein-coupled receptor proteins whose ligands could be roughly estimated, and in particular when homology to the known G protein-coupled receptor protein family is low, there is no or less information on the ligand, and estimation of the ligand was difficult.

As one of reported organ G protein-coupled receptors, there is APJ (O'Dowd, B. F., et al., Gene, 436, 355-359, 1993). APJ has low homology to angiotensin receptor (AT1). A naturally occurring ligand for APJ, and its partial peptides, are described in Biochemical and Biophysical Research Communications, 251, 471-476 (1998), WO 99/33976 (Japanese Patent Application No. 220853/1998), etc., but there is no known ligand derived from a naturally occurring ligand by artificial modifications (for example, a modified ligand wherein one to several constituent amino acids in a naturally occurring ligand are replaced by other amino acids, or side chains of one to several constituent amino acids in a naturally occurring ligand are substituted with suitable substituent groups).

DISCLOSURE OF INVENTION

A peptide prepared by artificially modifying a naturally occurring ligand for APJ that is an orphan G protein-coupled receptor expressed in the central nervous system, circulatory organ system, generative organ system, immune system, digestive organ system, etc. is considered more useful as a pharmaceutical preparation, etc. than the naturally occurring ligand, but the structure and functions of such a peptide more useful as a pharmaceutical preparation, etc. than the naturally occurring ligand have still not been revealed.

Based on this problem, the present inventors synthesized a wide variety of peptides by using, as an indicator, a change in the binding property between peptides which are modified derivatives of the naturally occurring ligand and the receptor protein, and estimated and specified an active site of the naturally occurring ligand, and as a result, the present inventors found modified derivatives of the naturally occurring ligand, which are more useful as a pharmaceutical preparation, etc.

That is, the present invention provides:

(1) a peptide represented by the formula:

P1-Arg-Pro-Arg-Leu-Phe-P2-P3-Gly-Pro-P4-P5 (I) (SEQ ID NO: 73)

wherein P1 represents a hydrogen atom, or an amino acid residue or a peptide chain, consisting of 1 to 25 amino acids which may be the same or different and whose side chain may be substituted, P2 represents a neutral amino acid residue whose side chain may be substituted or a basic amino acid residue whose side chain may be substituted, P3 represents a neutral amino acid residue whose side chain may be substituted, an aromatic amino acid residue whose side chain may be substituted or a basic amino acid residue whose side chain may be substituted, P4 represents a bond or a neutral or aromatic amino acid residue whose side chain may be substituted, P5 represents [1] an amino acid residue whose side chain may be substituted, or its amino acid derivative wherein the C-terminal carboxyl group has been reduced to a hydroxymethyl group or formyl group, [2] a hydroxyl group, or [3] a dipeptide chain formed by binding an amino acid residue whose side chain may be substituted, to an amino acid residue whose side chain may be substituted, or its peptide derivative wherein the C-terminal carboxyl group has been reduced to a hydroxymethyl group or formyl group, and a side chain of each amino acid residue in the formula -Arg-Pro-Arg-Leu-Phe- (SEQ ID NO: 74) or -Gly-Pro- may be substituted, an ester thereof or an amide thereof, or a salt thereof, (2) the peptide according to the above-mentioned (1), an ester thereof or an amide thereof, or a salt thereof, wherein P1 is a hydrogen atom, pGlu or Arg-Arg-Gln, (3) the peptide according to the above-mentioned (1), an ester thereof or an amide thereof, or a salt thereof, wherein P2 is optionally substituted His or optionally substituted Ala, (4) the peptide according to the above-mentioned (1), an ester thereof or an amide thereof, or a salt thereof, wherein P3 is optionally substituted Arg or optionally substituted Lys, (5) the peptide according to the above-mentioned (1), an ester thereof or an amide thereof, or a salt thereof, wherein -P4-P5 is -Cha-Pro-Phe(Cl), -Cha-Pro-Phe, -Met-Pro-Phe, -Met-Pro-Phe(Cl), -Cha-Phe or -Met-Phe, (6) the peptide according to the above-mentioned (1), which is represented by:

[1] Arg-Pro-Arg-Leu-Phe-Ala-Arg-Gly-Pro-Cha-Pro-Phe (Cl) (SEQ ID NO: 12),

[2] Arg-Pro-Arg-Leu-Phe-His-Lys-Gly-Pro-Cha-Pro-Phe (Cl) (SEQ ID NO: 13),

[3] Arg-Pro-Arg-Leu-Phe-His-Lys-Gly-Pro-Cha-Pro-Phe (SEQ ID NO: 15),

[4] Arg-Pro-Arg-Leu-Phe-His-Lys-Gly-Pro-Met-Pro-Phe (Cl) (SEQ ID NO: 16),

[5] Arg-Pro-Arg-Leu-Phe-Ala-Arg-Gly-Pro-Met-Pro-Phe (SEQ ID NO: 35),

[6] Arg-Pro-Arg-Leu-Phe-His-Lys-Gly-Pro-Cha-Phe(Cl) (SEQ ID NO: 41),

[7] pGlu-Arg-Pro-Arg-Leu-Phe-Arg-Arg-Gly-Pro-Met-Pro-Phe (SEQ ID NO: 46),

[8] pGlu-Arg-Pro-Arg-Leu-Phe-His-Lys-Gly-Pro-Met-Pro-Phe (SEQ ID NO: 48), or

[9] Arg-Pro-Arg-Leu-Phe-Ala-Arg-Gly-Pro-Met-Phe (SEQ ID NO: 51), an ester thereof or an amide thereof, or a salt thereof, (7) A peptide represented by the formula:

Q1-Arg-Pro-Arg-Leu-Ser-Ala-Q2-Gly-Q5-Q3-Q4 (II) (SEQ ID NO: 75)

wherein Q1 represents a hydrogen atom, or an amino acid residue or a peptide chain, consisting of 1 to 25 amino acids which may be the same or different and whose side chain may be substituted, Q2 represents a neutral amino acid residue whose side chain may be substituted, an aromatic amino acid residue whose side chain may be substituted or a basic amino acid residue whose side chain may be substituted, Q3 represents a bond or a neutral or aromatic amino acid residue whose side chain may be substituted, Q4 represents [1] an amino acid residue whose side chain may be substituted, or its amino acid derivative wherein the C-terminal carboxyl group has been reduced to a hydroxymethyl group or formyl group, [2] a hydroxyl group, or [3] a dipeptide chain formed by binding an amino acid residue whose side chain may be substituted, to an amino acid residue whose side chain may be substituted, or its peptide derivative wherein the C-terminal carboxyl group has been reduced to a hydroxymethyl group or formyl group, Q5 represents a neutral amino acid residue whose side chain may be substituted, and a side chain of each amino acid residue in the formula -Arg-Pro-Arg-Leu-Ser-Ala-(SEQ ID NO: 76) may be substituted, or an ester thereof or an amide thereof, or a salt thereof, (8) the peptide according to the above-mentioned (7), an ester thereof or an amide thereof, or a salt thereof, wherein Q1 is a hydrogen atom, pGlu or Arg-Arg-Gln, (9) the peptide according to the above-mentioned (7), an ester thereof or an amide thereof, or a salt thereof, wherein Q2 is optionally substituted Arg or optionally substituted Lys,

(10) the peptide according to the above-mentioned (7), an ester thereof or an amide thereof, or a salt thereof, wherein -Q3-Q4 is —OH, -Met, -Met-Pro-Phe, -Met-Pro-Phe (Cl), -Cha-Pro-Phe, -Cha-Pro-Phe(Cl), -Ala-Pro-Phe(Cl), -Cha-Phe-(Cl) or -Cha,

(11) the peptide according to the above-mentioned (7), an ester thereof or an amide thereof, or a salt thereof, wherein Q5 is optionally substituted Pro, optionally substituted Gly or optionally substituted Ala,

(12) the peptide according to the above-mentioned (7), which is represented by:

(i) Arg-Arg-Gln-Arg-Pro-Arg-Leu-Ser-Ala-Arg-Gly-Pro-Met-Pro-Phe(Cl) (SEQ ID NO: 1), (ii) Arg-Pro-Arg-Leu-Ser-Ala-Arg-Gly-Pro-Met-Pro-Phe (Cl) (SEQ ID NO: 3), (iii) Arg-Pro-Arg-Leu-Ser-Ala-Arg-Gly-Pro-Cha-Phe(Cl) (SEQ ID NO: 4), (iv) Arg-Pro-Arg-Leu-Ser-Ala-Arg-Gly-Pro-Cha-Pro-Phe (Cl) (SEQ ID NO: 5), (v) Arg-Arg-Gln-Arg-Pro-Arg-Leu-Ser-Ala-Arg-Gly-Pro-Cha (SEQ ID NO: 6), (vi) Arg-Pro-Arg-Leu-Ser-Ala-Arg-Gly-Pro-Cha-Pro-Phe (SEQ ID NO: 11), (vii) Arg-Arg-Gln-Arg-Pro-Arg-Leu-Ser-Ala-Arg-Gly-Pro-Met-Pro-Phe (SEQ ID NO: 21), (viii) Arg-Arg-Gln-Arg-Pro-Arg-Leu-Ser-Ala-Arg-Gly-Pro-Met (SEQ ID NO: 22), (ix) Arg-Arg-Gln-Arg-Pro-Arg-Leu-Ser-Ala-Arg-Gly-Pro (SEQ ID NO: 23), (x) Arg-Pro-Arg-Leu-Ser-Ala-Arg-Gly-Pro-Met-Pro-Phe (SEQ ID NO: 28), (xi) pGlu-Arg-Pro-Arg-Leu-Ser-Ala-Arg-Gly-Pro-Met-Pro-Phe (SEQ ID NO: 30), (xii) Arg-Pro-Arg-Leu-Ser-Ala-Arg-Gly-Pro-Met (SEQ ID NO: 31), (xiii) pGlu-Arg-Pro-Arg-Leu-Ser-Ala-Lys-Gly-Pro-Met-Pro-Phe (SEQ ID NO: 33), (xiv) Arg-Pro-Arg-Leu-Ser-Ala-Arg-Gly-Pro-Ala-Pro-Phe (Cl) (SEQ ID NO: 57), (xv) Arg-Pro-Arg-Leu-Ser-Ala-Arg-Gly-Gly-Met-Pro-Phe (Cl) (SEQ ID NO: 58), (xvi) Arg-Pro-Arg-Leu-Ser-Ala-Arg-Gly-NMe-Ala-Met-Pro-Phe(Cl) (SEQ ID NO: 59), (xvii) Arg-Pro-Arg-Leu-Ser-Ala-Arg-Gly-Pro-Cha-Pyn (SEQ ID NO: 64), (xviii) Arg-Pro-Arg-Leu-Ser-Ala-Arg-Gly-Pro-Cha-Pro-Pyn (SEQ ID NO: 65), (xix) Arg-Arg-Gln-Arg-Pro-Arg-Leu-Ser-Ala-Arg-Gly-Gly-Cha (SEQ ID NO: 66), or (xx) Arg-Pro-Arg-Leu-Ser-Ala-Lys(Me)$_2$-Gly-Pro-Met-Pro-Phe (SEQ ID NO: 68), an ester thereof or an amide thereof, or a salt thereof,

(13) a peptide represented by the formula:

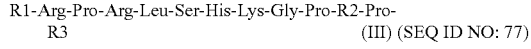

(III) (SEQ ID NO: 77)

wherein R1 represents a hydrogen atom, or an amino acid residue or a peptide chain, consisting of 1 to 25 amino acids which may be the same or different and whose side chain may be substituted, R2 represents optionally substituted Cha, optionally substituted Met or optionally substituted Nle, R3 represents optionally substituted Phe (Cl), optionally substituted Phe, optionally substituted Nal (2), optionally substituted Cha or optionally substituted Tyr, and a side chain of each amino acid residue in the formula -Arg-Pro-Arg-Leu-Ser-His-Lys-Gly-Pro-(SEQ ID NO: 78) or -Pro- may be substituted, an ester thereof or an amide thereof, or a salt thereof,

(14) the peptide according to the above-mentioned (13), an ester thereof or an amide thereof, or a salt thereof, wherein R1 is a hydrogen atom, pGu or Arg-Arg-Gln,

(15) the peptide according to the above-mentioned (13), which is represented by:

[1] Arg-Arg-Gln-Arg-Pro-Arg-Leu-Ser-His-Lys-Gly-Pro-Cha-Pro-Phe(Cl) (SEQ ID NO: 2),

[2] Arg-Pro-Arg-Leu-Ser-His-Lys-Gly-Pro-Cha-Pro-Phe (Cl) (SEQ ID NO: 7),

[3] Arg-Pro-Arg-Leu-Ser-His-Lys-Gly-Pro-Met-Pro-Phe (Cl) (SEQ ID NO: 8),

[4] pGlu-Arg-Pro-Arg-Leu-Ser-His-Lys-Gly-Pro-Cha-Pro-Phe (SEQ ID NO: 9),

[5] pGlu-Arg-Pro-Arg-Leu-Ser-His-Lys-Gly-Pro-Met-Pro-Phe(Cl) (SEQ ID NO: 10),

[6] Arg-Arg-Gln-Arg-Pro-Arg-Leu-Ser-His-Lys-Gly-Pro-Nle-Pro-Tyr (SEQ ID NO: 14),

[7] Arg-Pro-Arg-Leu-Ser-His-Lys-Gly-Pro-Met-Pro-Nal(2) (SEQ ID NO: 36),

[8] pGlu-Arg-Pro-Arg-Leu-Ser-His-Lys-Gly-Pro-Met-Pro-Nal(2) (SEQ ID NO: 43), or

[9] Arg-Pro-Arg-Leu-Ser-His-Lys-Gly-Pro-Met-Pro-Cha (SEQ ID NO: 53), an ester thereof or an amide thereof, or a salt thereof,

(16) a peptide represented by:

(i) Arg-Arg-Gln-Arg-Pro-Arg-Leu-Ser-His-Lys-Gly-Pro-Met(O) (SEQ ID NO: 24), (ii) Arg-Arg-Lys(Arg-Arg)-Arg-Pro-Arg-Leu-Ser-His-Lys-Gly-Pro-Met-Pro-Phe (SEQ ID NO: 25), (iii) Arg-Arg-Arg-Arg-Pro-Arg-Leu-Ser-His-Lys-Gly-Pro-Met-Pro-Phe (SEQ ID NO: 26), (iv) Arg-Arg-Lys-Arg-Pro-Arg-Leu-Ser-His-Lys-Gly-Pro-Met-Pro-Phe (SEQ ID NO: 27), (v) Arg-Arg-Ala-Arg-Pro-Arg-Leu-Ser-His-Lys-Gly-Pro-Met-Pro-Phe (SEQ ID NO: 29), (vi) Arg-Pro-Arg-Leu-Ser-His-Lys-Gly-Pro-Met-Phe(Cl) (SEQ ID NO: 32), (vii) pGlu-Arg-Pro-Arg-Leu-Ser-Arg-Lys-Gly-Pro-Met-Pro-Phe (SEQ ID NO: 34), (viii) Arg-Arg-Phe-Arg-Pro-Arg-Leu-Ser-His-Lys-Gly-Pro-Met-Pro-Phe (SEQ ID NO: 37), (ix) pGlu-Arg-Pro-Arg-Leu-Ser-His-Arg-Gly-Pro-Met-Pro-Phe (SEQ ID NO: 38), (x) pGlu-Arg-Pro-Arg-Leu-Ser-His-Lys-Gly-Pro-Met-Phe (Cl) (SEQ ID NO: 39), (xi) Arg-Pro-Arg-Leu-Ser-His-Lys-Gly-Pro-Met-Cha (SEQ ID NO: 40), (xii) pGlu-Arg-Pro-Arg-Leu-Ser-Leu-Lys-Gly-Pro-Met-Pro-Phe (SEQ ID NO: 42), (xiii) Arg-Pro-Arg-Leu-Ser-His-Lys-Gly-Pro-Met-Nal(2) (SEQ ID NO: 44), (xiv) pGlu-Arg-Pro-Arg-Leu-Ser-Arg-Arg-Gly-Pro-Met-Pro-Phe (SEQ ID NO: 45), (xv) pGlu-Arg-Pro-Arg-Leu-Ser-Phe-Lys-Gly-Pro-Met-Pro-Phe (SEQ ID NO: 47), (xvi) pGlu-Arg-Pro-Arg-Leu-Ser-His-Lys-Gly-Pro-Met-Cha (SEQ ID NO: 49), (xvii) pGlu-Arg-Pro-Arg-Leu-Ser-His-Lys-Gly-Pro-Met-Nal(2) (SEQ ID NO: 50), (xviii) pGlu-Arg-Pro-Arg-Leu-Ser-His-Phe-Gly-Pro-Met-Pro-Phe (SEQ ID NO: 52), (xix) pGlu-Arg-Pro-Arg-Leu-Ser-His-Leu-Gly-Pro-Met-Pro-Phe (SEQ ID NO: 54), (xx) Arg-Arg-Gln-Arg-Pro-Arg-Leu-Ser-Ala-Arg-Gly-NMe2 (SEQ ID NO: 55), (xxi) Arg-Arg-Gln-Arg-Pro-Arg-Leu-Ser-Ala-Arg-Gly-Mor (SEQ ID NO: 56), (xxii) Arg-Pro-Arg-Leu-Ser-His-Ala-Gly-Pro-Cha-Pro-Phe (Cl) (SEQ ID NO: 60), (xxiii) Arg-Pro-Arg-Ala-Ser-His-Lys-Gly-Pro-Cha-Pro-Phe (Cl) (SEQ ID NO: 61), (xxiv) Arg-Pro-Lys(Me)$_2$-Leu-Ser-Ala-Arg-Gly-Pro-Met-Pro-Phe (SEQ ID NO: 67), (xxv) Arg-Pro-Arg-Leu-Ser-Dap-Arg-Gly-Pro-Cha-Pro-Phe (Cl) (SEQ ID NO: 69), (xxvi) Arg-Pro-Arg-Leu-Ser-Dap(Ac)-Arg-Gly-Pro-Cha-Pro-Phe(Cl) (SEQ ID NO: 70), (xxvii) Arg-Pro-Arg-Leu-Ser-Dap(C6)-Arg-Gly-Pro-Cha-Pro-Phe(Cl) (SEQ ID NO: 71), (xxviii) Arg-Pro-Arg-Leu-Ser-Dap(Adi)-Arg-Gly-Pro-Cha-Pro-Phe(Cl) (SEQ ID NO: 72), or (xxix) Arg-Pro-Ala-Leu-Ser-His-Lys-Gly-Pro-Cha-Pro-Phe (Cl) (SEQ ID NO: 62), an ester thereof or an amide thereof, or a salt thereof,

(17) a pharmaceutical preparation comprising the peptide described in the above-mentioned (1), the above-mentioned (7), the above-mentioned (13) or the above-mentioned (16), an ester thereof or an amide thereof, or a salt thereof,

(18) the pharmaceutical preparation according to the above-mentioned (17), which is a neutral nerve function regulator, a circulatory function regulator, a cardiac function regulator, an immune function regulator, a digestive organ function regulator, a metabolic function regulator or a generative organ regulator,

(19) the pharmaceutical preparation according to the above-mentioned (17), which is a prophylactic and therapeutic agent for HIV infections or AIDS,

(20) the pharmaceutical preparation according to the above-mentioned (17), which is an agonist to a protein or a salt thereof having the amino acid sequence represented by SEQ ID NO:19,

(21) use of the peptide descried in the above-mentioned (1), the above-mentioned (7), the above-mentioned (13) or the above-mentioned (16), an ester thereof or an amide thereof, or a salt thereof in producing a pharmaceutical preparation comprising the peptide described in the above-mentioned (1), the above-mentioned (7), the above-mentioned (13) or the above-mentioned (16), an ester thereof or an amide thereof, or a salt thereof, and

(22) a method of preventing and treating HIV infections or AIDS, characterized in that the peptide described in the above-mentioned (1), the above-mentioned (7), the above-mentioned (13) or the above-mentioned (16), an ester thereof or an amide thereof, or a salt thereof is administered into mammalians.

Further, the present invention provides (23) the pharmaceutical preparation according to the above-mentioned (17), which is a prophylactic and/or therapeutic agent for dementia, melancholia, attention deficit hyperactivity (minimal brain disease) syndrome, mental confusion, anxiety, schizophrenia, psychasthenia, an obstacle in growth hormone secretion, bulimia, overeating, hypercholesterolemia, hyperglyceridemia, hyperlipemia, hyperprolactinemia, diabetes, cancers, pancreatitis, renal diseases, Turner's syndrome, neurosis, rheumatic arthritis, spinal damage, transitory cerebral ischemia paroxysm, amyotrophic lateral sclerosis, acute myocardial infarction, spinal cerebellum degeneration, bone fracture, wounds, atopic dermatitis, osteoporosis, asthma, epilepsy, sterility, arteriosclerosis, pulmonary emphysema, lung edema, imperfect lactation, or the like.

BEST MODE FOR CARRYING OUT THE INVENTION

The amino acid residue in the present invention refers to a structure excluding its N- or C-terminus, wherein the amino acid has lost a water molecule to form a peptide linkage through which it has been incorporated into a protein or a peptide. For example, the α-amino acid residue refers to the structure —HNC($R^0$)($R^1$)CO— excluding its N- or C-terminus, wherein the α-amino acid (H$_2$NC($R^0$)($R^1$)COOH wherein $R^0$ and $R^1$ are the same or different and represent an arbitrary substituent group) has lost a water molecule to form a peptide linkage through which it has been incorporated into a protein or a peptide. On one hand, the N-terminal amino acid residue is represented by H$_2$NC($R^0$)($R^1$)CO— and the C-terminal amino acid residue by —HNC($R^0$)($R^1$)COOH. The β-amino acid residue refers to the structure —HNC($R^0$)($R^1$)C($R^2$)($R^3$)CO— excluding its N- or C-terminus, wherein the β-amino acid (H$_2$NC($R^0$)($R^1$)C($R^2$)($R^3$)COOH wherein $R^0$, $R^1$, $R^2$ and $R^3$ are the same or different and represent an arbitrary substituent group) has lost a water molecule to form a peptide linkage through which it has been incorporated into a protein or a peptide. On one hand, the N-terminal amino acid residue is represented by H$_2$NC($R^0$)($R^1$)C($R^2$)($R^3$)CO— and the C-terminal amino acid residue by —NHC($R^0$)($R^1$)C($R^2$)($R^3$)COOH. The γ-amino acid residue refers to the structure —NHC($R^0$)($R^1$)C($R^2$)($R^3$)C($R^4$)($R^5$)CO— excluding its N- or C-terminus, wherein the γ-amino acid (H$_2$NC($R^0$)($R^1$)C($R^2$)($R^3$)C($R^4$)($R^5$)COOH wherein $R^0$, $R^1$, $R^2$, $R^3 R^4$ and $R^5$ are the same or different and represent an arbitrary substituent group) has lost a water molecule to form a peptide linkage through which it has been incorporated into a protein or a peptide. On one hand, the N-terminal amino acid residue is represented by H$_2$NC($R^0$)($R^1$)C($R^2$)($R^3$)C($R^4$)($R^5$)CO— and the C-terminal amino acid residue by —NHC($R^0$)($R^1$)C($R^2$)($R^3$)C($R^4$)($R^5$)COOH. The ε-amino acid residue refers to the structure —NHC($R^0$)($R^1$)C($R^2$)($R^3$)C($R^4$)($R^5$)C($R^6$)($R^7$)C($R^8$)($R^9$)CO— excluding its N- or C-terminus, wherein the ε-amino acid (H$_2$NC($R^0$)($R^1$)C($R^2$)($R^3$)C($R^4$)($R^5$)C($R^6$)($R^7$)C($R^8$)($R^9$)COOH wherein $R^0$, $R^1$, $R^2$, $R^3 R^4$, $R^5$, $R^6$, $R^7$, $R^8$ and $R^9$ are the same or different and represent an arbitrary substituent group) has lost a water molecule to form a peptide linkage through which it has been incorporated into a protein or a peptide. On one hand, the N-terminal amino acid residue is represented by H$_2$NC($R^0$)($R^1$)C($R^2$)($R^3$)C($R^4$)($R^5$)C($R^6$)($R^7$)C($R^8$)($R^9$)CO— and the C-terminal amino acid residue by —HNC($R^0$)($R^1$)C($R^2$)($R^3$)C($R^4$)($R^5$)C($R^6$)($R^7$)C($R^8$)($R^9$)COOH.

In this specification, the amino acid may be any of natural or non-natural, D- or L- and α-, β-, γ- or ε-amino acids.

The group forming a side chain of α-amino acid, β-amino acid, γ-amino acid and ε-amino acid includes, for example, (1) a $C_{1-6}$ alkyl group (e.g., methyl, ethyl, n-propyl, isopropyl, n-butyl, isobutyl, sec-butyl, tert-butyl, n-pentyl, etc., preferably $C_{1-3}$ alkyl, etc.), (2) a cyano group, (3) a halogen (e.g., fluorine, chlorine, bromine, iodine, etc.), (4) a hydroxy-$C_{1-6}$ alkyl group (e.g., hydroxymethyl, hydroxyethyl, etc.), (5) a $C_{1-6}$ alkoxy group (e.g., methoxy, ethoxy, n-propoxy, isopropoxy, n-butoxy, tert-butoxy, etc., preferably $C_{1-3}$ alkoxy, etc.), (6) a $C_{1-6}$ alkoxy-carbonyl group (e.g., methoxy carbonyl, ethoxy carbonyl, isopropoxy carbonyl, tert-butoxy carbonyl, etc., preferably $C_{1-3}$ alkoxy-carbonyl etc.), (7) a $C_{1-4}$ acyl group (e.g., formyl such as formyl, acetyl, propionyl, butyryl and $C_{2-4}$ alkanoyl, etc.), (8) a hydroxy group, (9) a group (e.g., methylthio, methanesulfinyl, methanesulfonyl, ethylthio, ethanesulfinyl, ethanesulfonyl, etc.) represented by the formula: $-S(O)a-R^{21}$ wherein a is an integer of 0 to 2, and $R^{21}$ represents a group represented by $C_{1-6}$ alkyl (which is specifically the same as described above), (10) benzyloxy carbonyl, (11) a tosyl group, (12) a carbamoyl group, (13) a mercapto group, (14) an amino group, (15) a sulfo group, (16) a phosphono group, (17) a phospho group, (18) a carboxyl group, (19) a tetrazolyl group, (20) an amino-$C_{1-6}$ alkyl group (e.g., aminomethyl, aminoethyl etc.), (21) an aminoallyl group, (22) a thiazolyl group, (23) a thienyl group, (24) an oxazolyl group, (25) a furyl group, (26) a pyranyl group, (27) a pyridyl group, (28) a pyrazyl group, (29) a pyrazinyl group, (30) a pyrimidinyl group, (31) a pyridazinyl group, (32) an indolyl group, (33) an indozinyl group, (34) an isoindolyl group, (35) a pyrrolyl group, (36) an imidazolyl group, (37) an isothiazolyl group, (38) a pyrazolyl group, (39) a chromenyl group, (40) a purinyl group, (41) a quinolizinyl group, (42) a quinolyl group, (43) an isoquinolyl group, (44) a quinazolinyl group, (45) a quinoxalinyl group, (46) a cinnolinyl group, (47) a morpholinyl group, (48) a benzothienyl group, (49) a benzofuranyl group, (50) benzimidazolyl, (51) a benzimidazolyl group, (52) a $C_{3-8}$ cycloalkyl group, (53) a $C_{1-4}$ alkyl group substituted with a substituent group described in the items (2), (3), (5) to (17), (20) to (52) above, (54) a $C_{1-4}$ acyl group such as formyl, $C_{2-4}$ alkanoyl etc. substituted with a substituent group described in the items (2), (3), (5) to (17), (20) to (52) above, (55) a $C_{6-10}$ aryl group (mesityl, tolyl, xylyl, styrenyl etc.) such as phenyl substituted with a substituent group described in the items (1) to (52) above, (56) a $C_{7-15}$ aralkyl group (methylbenzyl, methoxybenzyl etc.) such as benzyl substituted with a substituent group described in the items (1) to (52) above, (57) a $C_{7-15}$ aralkyl group (benzyl, phenethyl, benzhydryl, naphthylmethyl etc.), (58) a $C_{6-10}$ aryl group (phenyl, naphthyl, indenyl etc.), and (59) a hydrogen atom.

The side chain forming an amino acid residue may be bound to a nitrogen atom to form a ring (e.g., proline etc.), or 2 side chains are bound to each other to form a ring (e.g., 3-aminonorbornanecarboxylic acid etc.).

Examples of the α-amino acid include, for example, glycine, alanine, valine, leucine, isoleucine, serine, threonine, cysteine, methionine, aspartic acid, glutamic acid, lysine, arginine, phenylalanine, tyrosine, histidine, tryptophan, asparagine, glutamine, proline, pipecolic acid, norleucine, γ-methylleucine, tert-leucine, norvaline, homoarginine, homoserine, α-aminoisobutyric acid, α-aminobutyric acid, ornithine, α-aminoadipic acid, phenylglycine, thienylglycine, cyclohexylglycine, cyclohexylalanine, thienylalanine, naphthylalanine, biphenylalanine, p-phosphonomethylphenylalanine, octahydroindole-2-carboxylic acid, o-phosphotyrosine, adamantylalanine, benzothienylalanine, pyridylalanine, piperidylalanine, pyrazylalanine, quinolylalanine, thiazolylalanine, homocysteine, homophenylalanine, citrulline, homocitrulline, oxyproline (hydroxyproline), α,β-diaminopropionic acid, α,γ-diaminobutyric acid, aminomalonic acid, 1,2,3,4-tetrahydroisoquinoline-3-carboxylic acid, penicillamine, cycloleucine, 2-amino-4-pentenoic acid etc.

Examples of the β-amino acid include, for example, β-alanine, β-aminobutyric acid, isoasparagine, 3-aminoadipic acid, 3-aminophenylpropionic acid, 3-amino-2-hydroxy-4-phenylbutyric acid, 3-aminonorbornanecarboxylic acid, 3-aminobicycloheptanecarboxylic acid etc.

Examples of the γ-amino acid include, for example, γ-aminobutyric acid, isoglutamine, statine, 4-amino-3-hydroxy-5-cyclohexylpentanoic acid, 4-amino-3-hydroxy-5-phenylpentanoic acid, 6-aminopenicillaminic acid, 3-aminoadmantane-1-carboxylic acid etc.

Examples of the δ-amino acid include, for example, ε-aminocaproic acid, 4-aminomethyl-cyclohexanecarboxylic acid etc.

The natural amino acid includes glycine, alanine, valine, leucine, isoleucine, serine, threonine, cysteine, cystine, methionine, aspartic acid, glutamic acid, lysine, arginine, phenylalanine, tyrosine, histidine, tryptophan, asparagine, glutamine, proline, ornithine, citrulline etc.

The non-natural amino acid includes N-methylated amino acids derived from norleucine, γ-methylleucine, tert-leucine, norvaline, homoarginine, homoserine, aminoisobutyric acid, aminoadipic acid (e.g., α-aminoadipic acid), phenylglycine, thienylglycine, cyclohexylglycine, aminobutyric acid, β-alanine, cyclohexylalanine, thienylalanine, naphthylalanine, adamantylalanine, benzothienylalanine, pyridylalanine, piperidylalanine, pyridylalanine, quinolylalanine, thiazolylalanine, isoasparagine, isoglutamine, homocysteine, homophenylalanine, homocitrulline, oxyproline (hydroxyproline), diaminopropionic acid, diaminobutyric acid, aminobenzoic acid, the above-described natural amino acids and non-natural amino acids.

Examples of those substituent groups with which (side chains of) these amino acid residues may be substituted include (1) a $C_{1-6}$ alkyl group (e.g., methyl, ethyl, n-propyl, isopropyl, n-butyl, isobutyl, sec-butyl, tert-butyl, n-pentyl etc., preferably $C_{1-3}$ alkyl etc.), (2) a cyano group, (3) a halogen (e.g., fluorine, chlorine, bromine, iodine etc.), (4) a hydroxy-$C_{1-6}$ alkyl group (e.g., hydroxymethyl, hydroxyethyl etc.), (5) a $C_{1-6}$ alkoxy group (e.g., methoxy, ethoxy, n-propoxy, isopropoxy, n-butoxy, tert-butoxy etc., preferably $C_{1-3}$ alkoxy etc.), (6) a $C_{1-6}$ alkoxy-carbonyl group (e.g., methoxy carbonyl, ethoxy carbonyl, isopropoxy carbonyl, tert-butoxy carbonyl etc., preferably $C_{1-3}$ alkoxy-carbonyl etc.), (7) a $C_{1-4}$ acyl group (e.g., formyl, formyl such as acetyl, propionyl, butyryl and $C_{2-4}$ alkanoyl etc.), (8) a hydroxy group, (9) a group (e.g., methylthio, methanesulfinyl, methanesulfonyl, ethylthio, ethanesulfinyl, ethanesulfonyl etc.) represented by the formula: $-S(O)a-R^{21}$ wherein a is an integer of 0 to 2, and $R^{21}$ represents a group represented by $C_{1-6}$ alkyl (which is specifically the same as described above), (10) benzyloxy carbonyl, (11) a tosyl group, (12) a carbamoyl group, (13) a mercapto group, (14) an amino group, (15) a sulfo group, (16) a phosphono group, (17) a phospho group, (18) a carboxyl group, (19) a tetrazolyl group, (20) an amino-$C_{1-6}$ alkyl group (e.g., aminomethyl, aminoethyl etc.), (21) an aminoallyl group, (22) a thiazolyl group, (23) a thienyl group, (24) an oxazolyl group, (25) a furyl group, (26) a pyranyl group, (27) a pyridyl group, (28) a pyrazyl group, (29) a pyrazinyl group, (30) a pyrimidinyl group, (31) a pyridazinyl group, (32) an indolyl group, (33) an indozinyl group, (34) an isoindolyl group, (35) a pyrrolyl group, (36) an imidazolyl group, (37) an isothiazolyl group, (38) a pyrazolyl group, (39) a chromenyl group, (40) a purinyl group, (41) a quinolizinyl group, (42) a quinolyl group, (43) an isoquinolyl group, (44) a quinazolinyl group, (45) a quinoxalinyl group, (46) a cinnolinyl group, (47) a morpholinyl group, (48) a benzothienyl group, (49) a benzofuranyl group, (50) benzimidazolyl, (51) a benzimidazolyl group, (52) a $C_{3-8}$ cycloalkyl group, (53) an oxo group, (54) a $C_{1-4}$ alkyl group substituted with a substituent group described in the items (2), (3), (5) to (19), (22) to (52) above, (55) a $C_{1-4}$ acyl group such as formyl, $C_{2-4}$ alkanoyl etc. substituted with a substituent group described in the items (2), (3), (5) to (19), (22) to (52) above, (56) a $C_{6-10}$ aryl group (mesityl, tolyl, xylyl, styrenyl etc.) such as phenyl substituted with a substituent group described in the items (1) to (52) above, (57) a $C_{7-15}$ aralkyl group (methylbenzyl, methoxybenzyl etc.) such as benzyl substituted with a substituent group described in the items (1) to (52) above, (58) a $C_{7-15}$ aralkyl group (benzyl, phenethyl, benzhydryl, naphthylmethyl etc.), (59) a $C_{6-10}$ aryl group (phenyl, naphthyl, indenyl etc.), (60) an arginyl group, (61) a histidyl group and (62) an arginyl-arginyl group.

The neutral substituent group includes (1) a $C_{1-6}$ alkyl group (e.g., methyl, ethyl, n-propyl, isopropyl, n-butyl, isobutyl, sec-butyl, tert-butyl, n-pentyl etc., preferably $C_{1-3}$ alkyl etc.), (2) a cyano group, (3) a halogen (e.g., fluorine, chlorine, bromine, iodine etc.), (4) a hydroxy-$C_{1-6}$ alkyl group (e.g., hydroxymethyl, hydroxyethyl etc.), (5) a hydroxy group, (6) a carbamoyl group, (7) a mercapto group, (8) a group represented by the formula: —S(O)a—$R^{21}$ wherein each symbol has the same meaning as defined above, (9) a $C_{6-10}$ aryl group (e.g., phenyl, naphthyl, indenyl, chromenyl etc.), (10) a thienyl group, (11) an oxazolyl group, (12) a furyl group, (13) an indolyl group, (14) an indolizinyl group, (15) an isoindolyl group, (16) a $C_{3-8}$ cycloalkyl group, (17) an oxo group, (18) $C_{1-6}$ alkyl substituted with a substituent group described in the items (2), (3), (5) to (16) above, (19) a $C_{6-10}$ aryl group (mesityl, tolyl, xylyl, styrenyl etc.) such as phenyl, naphthyl etc. substituted with a substituent group described in the items (1) to (16) above, and (20) a $C_{7-15}$ aralkyl group (methylbenzyl, methoxybenzyl etc.) such as benzyl substituted with a substituent group described in the items (1) to (16) above.

The acidic substituent group includes a $C_{1-4}$ alkyl group, a $C_{6-10}$ aryl group such as phenyl and naphthyl, a $C_{7-15}$ aralkyl group such as benzyl, and a carbonyl group, each of which is substituted with a carboxyl group, sulfo group, tetrazolyl group etc.

The basic substituent group includes (1) an amino-$C_{1-6}$ alkyl group (aminomethyl, aminoethyl etc.), (2) an aminoallyl group, (3) a pyridyl group, (4) a pyradyl group, (5) a pyrazinyl group, (6) a pyridazinyl group, (7) an imidazolyl group, (8) a pyrazolyl group, (9) a pyrazolyl group, (10) a morpholinyl group, (11) an amino group, (12) a $C_{1-4}$ alkyl group substituted with a substituent group described in the items (3) to (10) above, (13) a $C_{7-15}$ aralkyl group such as benzyl substituted with a substituent group described in the items (1) to (11) above, (14) a $C_{6-10}$ aryl group such as phenyl, naphthyl etc. substituted with a substituent group described in the items (1) to (11) above, (15) an arginyl group, (16) a histidyl group and (17) an arginyl-arginyl group.

In this specification, the acidic amino acid (residue) is specifically an amino acid having an acidic group such as carboxyl group, sulfo group or tetrazolyl group in a side chain thereof. Examples thereof include glutamic acid, pyroglutamic acid, aspartic acid, cysteic acid, homocysteic acid, 3-(5-tetrazolyl) alanine, 2-amino-4-(5-tetrazolyl) butyric acid etc.

In this specification, the basic amino acid (residue) includes, for example, histidine, arginine, ornithine, lysine, diaminopropionic acid, diaminobutyric acid, homoarginine etc. Examples of the basic amino acid (residue) whose side chain has been substituted include, for example, $N^{\alpha}$-acetylarginine, $N^{\epsilon}$-tosylarginine, $N^{\epsilon}$-acetyllysine, $N^{\epsilon}$-methyllysine, $N^{\epsilon}$-tosyllysine etc.

In this specification, the neutral amino acid (residue) is specifically an amino acid such as alanine, valine, norvaline, leucine, isoleucine, alloisoleucine, norleucine, tertiary leucine, γ-methylleucine, proline, phenylglycine, phenylalanine, glutamine, asparagine, serine, threonine, glycine, cysteine, methionine, tryptophan, oxyproline (hydroxyproline), cyclohexylalanine and naphthylalanine.

In this specification, the amino acid (residue) having an aromatic side chain include, for example, tryptophan, phenylalanine, tyrosine, 1-naphthylalanine, 2-naphthylalanine, 2-thienylalanine, histidine, pyridylalanine (2-pyridylalanine), o-methyltyrosine etc. The amino acid (residue) having an aromatic side chain which has been substituted includes, for example, 3-iodotyrosine, p-phosphonomethylphenylalanine, o-phosphotyrosine etc.

In this specification, the amino acid (residue) having a hydroxy group in a side chain thereof includes, for example, serine, threonine, tyrosine, oxyproline (hydroxyproline) etc.

The peptide and peptide chain in this specification are represented in accordance with the conventional way of describing peptides, that is, the N-terminus (amino terminus) at the left hand and the C-terminus (carboxyl terminus) at the right hand. In the peptide and peptide chain of the present invention, the C-terminus is usually in the form of a carboxyl group (—COOH) or a carboxylate (—COO$^-$) but may be in the form of an amide (—CONH$_2$) or an ester (—COOR). Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, benzhydryl etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where the peptide of the present invention contains a carboxyl group or a carboxylate at a position other than the C-terminus, it may be amidated or esterified, and such an amide or ester is also included within the polypeptide of the present invention. As the ester, for example the C-terminal ester described above or the like is used.

Furthermore, examples of the peptide or peptide chains of the present invention include those peptide or peptide chains, wherein the amino group at the N-terminal amino acid residue of the peptide or peptide chain is protected with a substituent group (for example, [1] a $C_{1-8}$ acyl group such as a $C_{2-6}$ alkanoyl group, e.g., formyl group and acetyl, guanidinoacetyl, thienylacrylyl, pyridylacetyl etc., [2] a $C_{1-6}$ alkyl group such as methyl, ethyl, propyl, isopropyl, butyl, isobutyl, sec-butyl, tert-butyl, pentyl, hexyl etc., [3] a $C_{6-10}$ aryl group such as phenyl, naphthyl etc. or a $C_{7-16}$ aralkyl group such as benzyl, phenethyl etc., [4] a tosyl group, [5] a benzyloxycarbonyl group, [6] a group (e.g., methylthio, methanesulfinyl, methanesulfonyl, ethylthio, ethanesulfinyl, ethanesulfonyl etc.) represented by the formula: —S(O)a—$R^{22}$ wherein a is an integer of 0 to 2, and $R^{22}$ is a $C_{1-6}$ alkyl (which is specifically the same as described above), [7] a t-butoxycarbonyl group, [8] a N-9-fluorenyl methoxycarbonyl group etc.); those wherein the N-terminal region is cleaved in vivo and the glutamyl group thus formed is pyroglutaminated; those wherein a substituent (e.g., —OH, —SH, amino group, imidazolyl group, indolyl group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins bound to sugar chains.

In the above formula P1-Arg-Pro-Arg-Leu-Phe-P2-P3-Gly-Pro-P4-P5 (I) (SEQ ID NO: 73), Q1-Arg-Pro-Arg-Leu-Ser-Ala-Q2-Gly-Q5-Q3-Q4 (II) (SEQ ID NO: 75), and R1-Arg-Pro-Arg-Leu-Ser-His-Lys-Gly-Pro-R2-Pro-R3 (III) (SEQ ID NO: 77), (a side chain on each amino acid residue may be substituted, and the substituent group includes those described above.

In this specification, P1, Q1 and R1 represent "a hydrogen atom or amino acid residue, or a peptide chain, consisting of 1 to 25 amino acids which may be the same or different and whose side chain may be substituted".

The substituent groups on the "1 to 25 amino acids whose side chain may be substituted" include, for example, those identical with the "substituent groups with which side chains of these amino acid residues may be substituted".

When P1, Q1 and R1 represent the "amino acids whose side chain may be substituted", preferable examples thereof include, for example, optionally substituted pyroglutamic acid or glutamine whose side chain may be substituted, more preferably pyroglutamic acid or glutamine.

In the "amino acid residues whose side chain may be substituted", "optionally substituted pyroglutamic acid" and "glutamine whose side chain may be substituted", the substituent groups on the amino acid residues include, for example, those identical with the "substituent groups with which side chains of these amino acid residues may be substituted".

As a preferable substituent group on the "optionally substituted pyroglutamic acid", a benzyloxycaronyl group or the like is exemplified.

When P1, Q1 and R1 represent the "peptide chain consisting of 2 to 25 amino acids which may be the same or different and whose side chain may be substituted", examples thereof include, for example, peptides represented by the formula:

$$Y^1—Y^2$$

wherein $Y^1$ represents amino acid residues, or a peptide chain, consisting of 1 to 17 amino acids which may be the same or different and whose side chain may be substituted, and $Y^2$ represents amino acid residues, or a peptide chain, consisting of 1 to 8 amino acids which may be the same or different and whose side chain may be substituted.

The substituent groups on side chains of amino acid residues, or of amino acid residues in a peptide chain, represented by the above-mentioned $Y^1$ and $Y^2$ include, for example, those identical with the "substituent groups with which side chains of these amino acid residues may be substituted".

Examples of the above-mentioned $Y^1$ include, for example, amino acid residues or peptide chains represented by:

(a) the formula $A^1—A^2—A^3—A^4—A^5—A^6—A^7—A^8—A^9—A^{10}—A^{11}—A^{12}—A^{13}—A^{14}—A^{15}—A^{16}—A^{17}$ wherein $A^1$ to $A^{17}$ are the same or different and represent an amino acid residue whose side chain may be substituted, (b) the formula $A^2—A^3—A^4—A^5—A^6—A^7—A^8—A^9—A^{10}—A^{11}—A^{12}—A^{13}—A^{14}—A^{15}—A^{16}—A^{17}$ wherein each symbol has the same meaning as defined above, (c) the formula $A^3—A^4—A^5—A^6—A^7—A^8—A^9—A^{10}—A^{11}—A^{12}—A^{13}—A^{14}—A^{15}—A^{16}—A^{17}$ wherein each symbol has the same meaning as defined above, (d) the formula $A^4—A^5—A^6—A^7—A^8—A^9—A^{10}—A^{11}—A^{12}—A^{13}—A^{14}—A^{15}—A^{16}—A^{17}$ wherein each symbol has the same meaning as defined above, (e) the formula $A^5—A^6—A^7—A^8—A^9—A^{10}—A^{11}—A^{12}—A^{13}—A^{14}—A^{15}—A^{16}—A^{17}$ wherein each symbol has the same meaning as defined above, (f) the formula $A^6—A^7—A^8—A^9—A^{10}—A^{11}—A^{12}—A^{13}—A^{14}—A^{15}—A^{16}—A^{17}$ wherein each symbol has the same meaning as defined above, (g) the formula $A^7—A^8—A^9—A^{10}—A^{11}—A^{12}—A^{13}—A^{14}—A^{15}—A^{16}—A^{17}$ wherein each symbol has the same meaning as defined above, (h) the formula $A^8—A^9—A^{10}—A^{11}—A^{12}—A^{13}—A^{14}—A^{15}—A^{16}—A^{17}$ wherein each symbol has the same meaning as defined above, (i) the formula $A^9—A^{10}—A^{11}—A^{12}—A^{13}—A^{14}—A^{15}—A^{16}—A^{17}$ wherein each symbol has the same meaning as defined above, j) the formula $A^{10}—A^{11}—A^{12}—A^{13}—A^{14}—A^{15}—A^{16}—A^{17}$ wherein each symbol has the same meaning as defined above, (k) the formula $A^{11}—A^{12}—A^{13}—A^{14}—A^{15}—A^{16}—A^{17}$ wherein each symbol has the same meaning as defined above, (l) the formula $A^{12}—A^{13}—A^{14}—A^{15}—A^{16}—A^{17}$ wherein each symbol has the same meaning as defined above, (m) the formula $A^{13}—A^{14}—A^{15}—A^{16}—A^{17}$ wherein each symbol has the same meaning as defined above, (n) the formula $A^{14}—A^{15}—A^{16}—A^{17}$ wherein each symbol has the same meaning as defined above, (o) the formula $A^{15}—A^{16}—A^{17}$ wherein each symbol has the same meaning as defined above, (p) the formula $A^{16}—A^{17}$ wherein each symbol has the same meaning as defined above, and (q) the formula $A^{17}$ wherein $A^{17}$ has the same meaning as defined above.

The above-mentioned $A^1$ represents an amino acid residue whose side chain may be substituted, preferably an amino acid residue having an aromatic side chain, more preferably an L-amino acid residue having an aromatic side chain, still more preferably L-tyrosine.

The above-mentioned $A^2$ and $A^3$ are the same or different, and represent an amino acid residue whose side chain may be substituted, preferably a neutral amino acid residue whose side chain may be substituted, more preferably a neutral L-amino acid residue whose side chain may be substituted, and still more preferably $A^2$ is L-leucine or the like and $A^3$ is L-valine or the like.

The above-mentioned $A^4$ represents an amino acid residue whose side chain may be substituted, preferably a neutral or basic amino acid residue whose side chain may be substituted, more preferably a neutral or basic L-amino acid residue whose side chain may be substituted, still more preferably L-lysine or $N^8$-acetyllysine.

The above-mentioned $A^5$ represents an amino acid residue whose side chain may be substituted, preferably a neutral amino acid residue whose side chain may be substituted, more preferably optionally substituted L-proline, still more preferably L-proline or the like.

The above-mentioned $A^6$ and $A^9$ are the same or different, and represent an amino acid residue whose side chain may be substituted, preferably a basic amino acid residue whose side chain may be substituted, more preferably a basic L-amino acid residue whose side chain may be substituted, still more preferably L-arginine or the like.

The above-mentioned $A^7$ and $A^{10}$ are the same or different, and represent an amino acid residue whose side chain may be substituted, preferably an amino acid residue having a hydroxy group in a side chain thereof or a neutral amino acid residue whose side chain may be substituted.

As $A^7$, optionally substituted glycine, particularly glycine or the like, is preferably used.

The above-mentioned $A^8$ represents an amino acid residue whose side chain may be substituted, preferably L-proline and an amino acid residue having a hydroxy group in a side chain thereof, more preferably L-serine, L-proline or oxyproline (hydroxyproline).

The above-mentioned $A^{10}$ represents an amino acid residue having a hydroxy group in a side chain thereof or a neutral amino acid residue whose side chain may be substituted, more preferably serine, threonine, asparagine etc.

The above-mentioned $A^{11}$ and $A^{14}$ are the same or different, and represent an amino acid residue whose side chain may be substituted, preferably a neutral amino acid residue whose side chain may be substituted, and more preferably $A^{11}$ is glycine, $A^{12}$ is L-proline, $A^{13}$ is glycine, $A^{14}$ is L-alanine, L-proline or the like.

The above-mentioned $A^{15}$ represents an amino acid residue whose side chain may be substituted, preferably an amino acid residue having an aromatic side chain, more preferably an L-amino acid residue having an aromatic side chain, still more preferably L-tryptophan.

The above-mentioned $A^{16}$ represents an amino acid residue whose side chain may be substituted, preferably a neutral amino acid residue whose side chain may be substituted, more preferably a neutral L-amino acid residue having a carbamoyl group, still more preferably L-glutamine.

The neutral L-amino acid residue having a carbamoyl group includes, for example, L-glutamine, L-asparagine etc.

The above-mentioned $A^{17}$ represents an amino acid residue whose side chain may be substituted, preferably a neutral amino acid residue whose side chain may be substituted, more preferably glycine etc.

Examples of the above-mentioned $Y^2$ include, for example, amino acid residues or peptide chains represented by:

[1] the formula $B^1$—$B^2$—$B^3$—$B^4$—$B^5$—$B^6$—$B^7$—$B^8$ wherein $B^1$ to $B^8$ are the same or different, and represent an amino acid residue whose side chain may be substituted,

[2] the formula $B^2$—$B^3$—$B^4$—$B^5$—$B^6$—$B^7$—$B^8$ wherein each symbol has the same meaning as defined above,

[3] the formula $B^3$—$B^4$—$B^5$—$B^6$—$B^7$—$B^8$ wherein each symbol has the same meaning as defined above,

[4] the formula $B^4$—$B^5$—$B^6$—$B^7$—$B^8$ wherein each symbol has the same meaning as defined above,

[5] the formula $B^5$—$B^6$—$B^7$—$B^8$ wherein each symbol has the same meaning as defined above,

[6] the formula $B^6$—$B^7$—$B^8$ wherein each symbol has the same meaning as defined above,

[7] the formula $B^7$—$B^8$ wherein each symbol has the same meaning as defined above, and

[8] the formula $B^8$ wherein $B^8$ has the same meaning as defined above.

The above-mentioned $B^1$ represents an amino acid residue whose side chain may be substituted, preferably a neutral amino acid residue whose side chain may be substituted, more preferably a neutral L-amino acid residue whose side chain may be substituted, still more preferably optionally substituted glycine, most preferably glycine.

The above-mentioned $B^2$ to $B^4$ are the same or different, and represent an amino acid residue whose side chain may be substituted, preferably a basic amino acid residue whose side chain may be substituted, more preferably a basic L-amino acid residue whose side chain may be substituted, and still more preferably $B^2$ is L-arginine, $B^3$ is L-arginine, and $B^4$ is L-lysine.

The above-mentioned $B^5$ represents an amino acid residue whose side chain may be substituted, preferably an amino acid residue having an aromatic side chain, more preferably an L-amino acid residue having an aromatic side chain, still more preferably L-phenylalanine.

The above-mentioned $B^6$ and $B^7$ are the same or different, and represent an amino acid residue whose side chain may be substituted, preferably a basic amino acid residue whose side chain may be substituted, more preferably a basic L-amino acid residue whose side chain may be substituted, further more preferably L-arginine.

The above-mentioned $B^8$ represents an amino acid residue whose side chain may be substituted, preferably glutamine whose side chain may be substituted, more preferably L-glutamine.

Combinations of $Y^1$ and $Y^2$ include:

the case of the formula represented by the above-mentioned (a)+the formula represented by the above-mentioned [1] (that is, the case where $X^1$ is represented by $A^1$—$A^2$—$A^3$—$A^4$—$A^5$—$A^6$—$A^7$—$A^8$—$A^9$—$A^{10}$—$A^{11}$—$A^{12}$—$A^{13}$—$A^{14}$—$A^{15}$—$A^{16}$—$A^{17}$—$B^1$—$B^2$—$B^3$—$B^4$—$B^5$—$B^6$—$B^7$—$B^8$; this will be omitted in the description of the following combinations), the case of the formula represented by the above-mentioned (a)+the formula represented by the above-mentioned [2], the case of the formula represented by the above-mentioned (a)+the formula represented by the above-mentioned [3], the case of the formula represented by the above-mentioned (a)+the formula represented by the above-mentioned [4], the case of the formula represented by the above-mentioned (a)+the formula represented by the above-mentioned [5], the case of the formula represented by the above-mentioned (a)+the formula represented by the above-mentioned [6], the case of the formula represented by the above-mentioned (a)+the formula represented by the above-mentioned [7], the case of the formula represented by the above-mentioned (a)+the formula represented by the above-mentioned [8], the case of the formula represented by the above-mentioned (b)+the formula represented by the above-mentioned [1], the case of the formula represented by the above-mentioned (b)+the formula represented by the above-mentioned [2], the case of the formula represented by the above-mentioned (b)+the formula represented by the above-mentioned [3], the case of the formula represented by the above-mentioned (b)+the formula represented by the above-mentioned [4], the case of the formula represented by the above-mentioned (b)+the formula represented by the above-mentioned [5], the case of the formula represented by the above-mentioned (b)+the formula represented by the above-mentioned [6], the case of the formula represented by the above-mentioned (b)+the formula represented by the above-mentioned [7], the case of the formula represented by the above-mentioned (b)+the formula represented by the above-mentioned [8], the case of the formula represented by the above-mentioned (c)+the formula represented by the above-mentioned [1], the case of the formula represented by the above-mentioned (c)+the formula represented by the above-mentioned [2], the case of the formula represented by the above-mentioned (c)+the formula represented by the above-mentioned [3], the case of the formula represented by the above-mentioned (c)+the formula represented by the above-mentioned [4], the case of the formula represented by the above-mentioned (c)+the formula represented by the above-mentioned [5], the case of the formula represented by the above-mentioned (c)+the formula represented by the above-mentioned [6], the case of the formula represented by the above-mentioned (c)+the formula represented by the above-mentioned [7], the case of the formula represented by the above-mentioned (c)+the formula represented by the above-mentioned [8], the case of the formula represented by the above-mentioned (d)+the formula represented by the above-mentioned [1], the case of the formula represented by the above-mentioned (d)+the formula represented by the above-mentioned [2], the case of the formula represented by the above-mentioned (d)+the formula represented by the above-mentioned [3], the case of the formula represented by the above-mentioned (d)+the formula represented by the above-mentioned [4], the case of the formula represented by the above-mentioned (d)+the formula represented by the above-mentioned [5], the case of the formula represented by the above-mentioned (d)+the formula represented by the above-mentioned [6], the case of the formula represented by the above-mentioned (d)+the formula represented by the above-mentioned [7], the case of the formula represented by the above-mentioned (d)+the formula represented by the above-mentioned [8], the case of the formula represented by the above-mentioned (e)+the formula represented by the above-mentioned [1], the case of the formula represented by the above-mentioned (e)+the formula represented by the above-mentioned [2], the case of the formula represented by the above-mentioned (e)+the formula represented by the above-mentioned [3], the case of the formula represented by the above-mentioned (e)+the formula represented by the above-mentioned [4], the case of the formula represented by the above-mentioned (e)+the formula represented by the above-mentioned [5], the case of the formula represented by the above-mentioned (e)+the formula represented by the above-mentioned [6], the case of the formula represented by the above-mentioned (e)+the formula represented by the above-mentioned [7], the case of the formula represented by the above-mentioned (e)+the formula represented by the above-mentioned [8], the case of the formula represented by the above-mentioned (f)+the formula represented by the above-mentioned [1], the case of the formula represented by the above-mentioned (f)+the formula represented by the above-mentioned [2], the case of the formula represented by the above-mentioned (f)+the formula represented by the above-mentioned [3], the case of the formula represented by the above-mentioned (f)+the formula represented by the above-mentioned [4], the case of the formula represented by the above-mentioned (f)+the formula represented by the above-mentioned [5], the case of the formula represented by the above-mentioned (f)+the formula represented by the above-mentioned [6], the case of the formula represented by the above-mentioned (f)+the formula represented by the above-mentioned [7], the case of the formula represented by the above-mentioned (f)+the formula represented by the above-mentioned [8], the case of the formula represented by the above-mentioned (g)+the formula represented by the above-mentioned [1], the case of the formula represented by the above-mentioned (g)+the formula represented by the above-mentioned [2], the case of the formula represented by the above-mentioned (g)+the formula represented by the above-mentioned [3], the case of the formula represented by the above-mentioned (g)+the formula represented by the above-mentioned [4], the case of the formula represented by the above-mentioned (g)+the formula represented by the above-mentioned [5], the case of the formula represented by the above-mentioned (g)+the formula represented by the above-mentioned [6], the case of the formula represented by the above-mentioned (g)+the formula represented by the above-mentioned [7], the case of the formula represented by the above-mentioned (g)+the formula represented by the above-mentioned [8], the case of the formula represented by the above-mentioned (h)+the formula represented by the above-mentioned [1], the case of the formula represented by the above-mentioned (h)+the formula represented by the above-mentioned [2], the case of the formula represented by the above-mentioned (h)+the formula represented by the above-mentioned [3], the case of the formula represented by the above-mentioned (h)+the formula represented by the above-mentioned [4], the case of the formula represented by the above-mentioned (h)+the formula represented by the above-mentioned [5], the case of the formula represented by the above-mentioned (h)+the formula represented by the above-mentioned [6], the case of the formula represented by the above-mentioned (h)+the formula represented by the above-mentioned [7], the case of the formula represented by the above-mentioned (h)+the formula represented by the above-mentioned [8], the case of the formula represented by the above-mentioned (i)+the formula represented by the above-mentioned [1], the case of the formula represented by the above-mentioned (i)+the formula represented by the above-mentioned [2], the case of the formula represented by the above-mentioned (i)+the formula represented by the above-mentioned [3], the case of the formula represented by the above-mentioned (i)+the formula represented by the above-mentioned [4], the case of the formula represented by the above-mentioned (i)+the formula represented by the above-mentioned [5], the case of the formula represented by the above-mentioned (i)+the formula represented by the above-mentioned [6], the case of the formula represented by the above-mentioned (i)+the formula represented by the above-mentioned [7], the case of the formula represented by the above-mentioned (i)+the formula represented by the above-mentioned [8], the case of the formula represented by the above-mentioned (j)+the formula represented by the above-mentioned [1], the case of the formula represented by the above-mentioned (j)+the formula represented by the above-mentioned [2], the case of the formula represented by the above-mentioned (j)+the formula represented by the above-mentioned [3], the case of the formula represented by the above-mentioned (j)+the formula represented by the above-mentioned [4], the case of the formula represented by the above-mentioned (j)+the formula represented by the above-mentioned [5], the case of the formula represented by the above-mentioned (j)+the formula represented by the above-mentioned [6], the case of the formula represented by the above-mentioned (j)+the formula represented by the above-mentioned [7], the case of the formula represented by the above-mentioned (j)+the formula represented by the above-mentioned [8], the case of the formula represented by the above-mentioned (k)+the formula represented by the above-mentioned [1], the case of the formula represented by the above-mentioned (k)+the formula represented by the above-mentioned [2], the case of the formula represented by the above-mentioned (k)+the formula represented by the above-mentioned [3], the case of the formula represented by the above-mentioned (k)+the formula represented by the above-mentioned [4], the case of the formula represented by the above-mentioned (k)+the formula represented by the above-mentioned [5], the case of the formula represented by the above-mentioned (k)+the formula represented by the above-mentioned [6], the case of the formula represented by the above-mentioned (k)+the formula represented by the above-mentioned [7], the case of the formula represented by the above-mentioned (k)+the formula represented by the above-mentioned [8], the case of the formula represented by the above-mentioned (l)+the formula represented by the above-mentioned [1], the case of the formula represented by the above-mentioned (l)+the formula represented by the above-mentioned [2], the case of the formula represented by the above-mentioned (l)+the formula represented by the above-mentioned [3], the case of the formula represented by the above-mentioned (l)+the formula represented by the above-mentioned [4], the case of the formula represented by the above-mentioned (l)+the formula represented by the above-mentioned [5], the case of the formula represented by the above-mentioned (l)+the formula represented by the above-mentioned [6], the case of the formula represented by the above-mentioned (l)+the formula represented by the above-mentioned [7], the case of the formula represented by the above-mentioned (l)+the formula represented by the above-mentioned [8], the case of the formula represented by the above-mentioned (m)+the formula represented by the above-mentioned [1], the case of the formula represented by the above-mentioned (m)+the formula represented by the above-mentioned [2], the case of the formula represented by the above-mentioned (m)+the formula represented by the above-mentioned [3], the case of the formula represented by the above-mentioned (m)+the formula represented by the above-mentioned [4], the case of the formula represented by the above-mentioned (m)+the formula represented by the above-mentioned [5], the case of the formula represented by the above-mentioned (m)+the formula represented by the above-mentioned [6], the case of the formula represented by the above-mentioned (m)+the formula represented by the above-mentioned [7], the case of the formula represented by the above-mentioned (m)+the formula represented by the above-mentioned [8], the case of the formula represented by the above-mentioned (n)+the formula represented by the above-mentioned [1], the case of the formula represented by the above-mentioned (n)+the formula represented by the above-mentioned [2], the case of the formula represented by the above-mentioned (n)+the formula represented by the above-mentioned [3], the case of the formula represented by the above-mentioned (n)+the formula represented by the above-mentioned [4], the case of the formula represented by the above-mentioned (n)+the formula represented by the above-mentioned [5], the case of the formula represented by the above-mentioned (n)+the formula represented by the above-mentioned [6], the case of the formula represented by the above-mentioned (n)+the formula represented by the above-mentioned [7], the case of the formula represented by the above-mentioned (n)+the formula represented by the above-mentioned [8], the case of the formula represented by the above-mentioned (o)+the formula represented by the above-mentioned [1], the case of the formula represented by the above-mentioned (o)+the formula represented by the above-mentioned [2], the case of the formula represented by the above-mentioned (o)+the formula represented by the above-mentioned [3], the case of the formula represented by the above-mentioned (o)+the formula represented by the above-mentioned [4], the case of the formula represented by the above-mentioned (o)+the formula represented by the above-mentioned [5], the case of the formula represented by the above-mentioned (o)+the formula represented by the above-mentioned [6], the case of the formula represented by the above-mentioned (o)+the formula represented by the above-mentioned [7], the case of the formula represented by the above-mentioned (o)+the formula represented by the above-mentioned [8], the case of the formula represented by the above-mentioned (p)+the formula represented by the above-mentioned [1], the case of the formula represented by the above-mentioned (p)+the formula represented by the above-mentioned [2], the case of the formula represented by the above-mentioned (p)+the formula represented by the above-mentioned [3], the case of the formula represented by the above-mentioned (p)+the formula represented by the above-mentioned [4], the case of the formula represented by the above-mentioned (p)+the formula represented by the above-mentioned [5], the case of the formula represented by the above-mentioned (p)+the formula represented by the above-mentioned [6], the case of the formula represented by the above-mentioned (p)+the formula represented by the above-mentioned [7], the case of the formula represented by the above-mentioned (p)+the formula represented by the above-mentioned [8], the case of the formula represented by the above-mentioned (q)+the formula represented by the above-mentioned [1], the case of the formula represented by the above-mentioned (q)+the formula represented by the above-mentioned [2], the case of the formula represented by the above-mentioned (q)+the formula represented by the above-mentioned [3], the case of the formula represented by the above-mentioned (q)+the formula represented by the above-mentioned [4], the case of the formula represented by the above-mentioned (q)+the formula represented by the above-mentioned [5], the case of the formula represented by the above-mentioned (q)+the formula represented by the above-mentioned [6], the case of the formula represented by the above-mentioned (q)+the formula represented by the above-mentioned [7], and the case of the formula represented by the above-mentioned (q)+the formula represented by the above-mentioned [8], among which particularly preferable are:

the case of the formula represented by the above-mentioned (a)+the formula represented by the above-mentioned [1], the case of the formula represented by the above-mentioned (b)+the formula represented by the above-mentioned [1], the case of the formula represented by the above-mentioned (c)+the formula represented by the above-mentioned [1], the case of the formula represented by the above-mentioned (d)+the formula represented by the above-mentioned [1], the case of the formula represented by the above-mentioned (e)+the formula represented by the above-mentioned [1], the case of the formula represented by the above-mentioned (f)+the formula represented by the above-mentioned [1], the case of the formula represented by the above-mentioned (g)+the formula represented by the above-mentioned [1], the case of the formula represented by the above-mentioned (h)+the formula represented by the above-mentioned [1], the case of the formula represented by the above-mentioned (i)+the formula represented by the above-mentioned [1], the case of the formula represented by the above-mentioned (j)+the formula represented by the above-mentioned [1], the case of the formula represented by the above-mentioned (k)+the formula represented by the above-mentioned [1], the case of the formula represented by the above-mentioned (l)+the formula represented by the above-mentioned [1], the case of the formula represented by the above-mentioned (m)+the formula represented by the above-mentioned [1], the case of the formula represented by the above-mentioned (n)+the formula represented by the above-mentioned [1], the case of the formula represented by the above-mentioned (o)+the formula represented by the above-mentioned [1], the case of the formula represented by the above-mentioned (p)+the formula represented by the above-mentioned [1], and the case of the formula represented by the above-mentioned (q)+the formula represented by the above-mentioned [1].

In particular, the case of the formula represented by the above-mentioned (a)+the formula represented by the above-mentioned [1] and the case of the formula represented by the above-mentioned (b)+the formula represented by the above-mentioned [1] are mentioned as more preferable examples.

Still more preferable examples of the case of the formula represented by the above-mentioned (a)+the formula represented by the above-mentioned [1] and the case of the formula represented by the above-mentioned (b)+the formula represented by the above-mentioned [1] are shown below.

The case of the formula represented by the above-mentioned (b)+the formula represented by the above-mentioned [1] refers to the case where P1, Q1 and/or R1 is represented by the formula $A^2—A^3—A^4—A^5—A^6—A^7—A^8—A^9—A^{10}—A^{11}—A^{12}—A^{13}—A^{14}—A^{15}—A^{16}—A^{17}—B^1—B^2—B^3—B^4—B^5—B^6—B^7—B^8$ wherein $A^2$ to $A^{17}$ and $B^1$ to $B^8$ have the same meaning as defined above, and in preferable examples in this case, $A^2$ and $A^3$ are the same or different, and represent a neutral L-amino acid residue whose side chain may be substituted, and preferably $A^2$ is L-leucine or the like and $A^3$ is L-valine or the like, $A^4$ is a neutral or basic L-amino acid residue whose side chain may be substituted, preferably L-glutamine, L-lysine or $N^\epsilon$-acetyllysine, $A^5$ is L-proline whose side chain may be substituted, preferably L-proline or the like, $A^6$ and $A^9$ are the same or different, and represent a basic L-amino acid residue whose side chain may be substituted, preferably L-arginine, $A^7$ is optionally substituted glycine, preferably glycine or the like, $A^8$ is L-proline or an amino acid residue having a hydroxy group in a side chain thereof, preferably L-serine, L-proline or oxyproline (hydroxyproline), $A^{10}$ is an amino acid residue having a hydroxy group in a side chain thereof or a neutral amino acid residue whose side chain may be substituted, preferably L-serine, L-threonine, L-asparagine or the like, $A^{11}$ is glycine, $A^{12}$ is L-proline, $A^{13}$ is glycine, and $A^{14}$ is L-alanine or L-proline, $A^{15}$ is an L-amino acid residue having an aromatic side chain, preferably L-tryptophan or the like, $A^{16}$ is a neutral L-amino acid residue having a carbamoyl group, preferably L-glutamine, $A^{17}$ is a neutral amino acid residue, preferably glycine, $B^1$ is a neutral L-amino acid residue whose side chain may be substituted, preferably optionally substituted glycine, more preferably glycine or the like, $B^2$ and $B^4$ are the same or different, and represent a basic L-amino acid residue whose side chain may be substituted, and preferably $B^2$ is L-arginine, $B^3$ is L-arginine, and $B^4$ is L-lysine, $B^5$ is an L-amino acid residue having an aromatic side chain, preferably L-phenylalanine or the like, $B^6$ and $B^7$ are the same or different, and represent a basic L-amino acid residue whose side chain may be substituted, preferably L-arginine or the like, and $B^8$ is glutamine whose side chain may be substituted, preferably L-glutamine or the like.

The case of the formula represented by the above-mentioned (a)+the formula represented by the above-mentioned [1] refers to the case where $X^1$ is represented by the formula $A^1—A^2—A^3—A^4—A^5—A^6—A^7—A^8—A^9—A^{10}—A^{11}—A^{12}—A^{13}—A^{14}—A^{15}—A^{16}—A^{17}—B^1—B^2—B^3—B^4—$ $B^5$—$B^6$—$B^7$—$B^8$ wherein $A^1$ to $A^{17}$ and $B^1$ to $B^8$ have the same meaning as defined above, and in preferable examples in this case, $A^1$ is an L-amino acid residue having an aromatic side chain, more preferably L-tyrosine or the like, $A^2$ and $A^3$ are the same or different, and represent a neutral L-amino acid residue whose side chain may be substituted, and preferably $A^2$ is L-leucine or the like, and $A^3$ is L-valine or the like, $A^4$ is a neutral or basic L-amino acid residue whose side chain may be substituted, preferably L-glutamine, L-α-aminoadipic acid, L-lysine or $N^ε$-acetyllysine, $A^5$ is L-proline whose side chain may be substituted, preferably L-proline or the like, $A^6$ and $A^9$ are the same or different, and represent a basic L-amino acid residue whose side chain may be substituted, preferably L-arginine or the like, $A^7$ is optionally substituted glycine, preferably glycine or the like, $A^8$ is L-proline or an amino acid residue having a hydroxy group in a side chain thereof, preferably L-serine, L-proline or oxyproline (hydroxyproline), $A^{10}$ is an amino acid residue having a hydroxy group in a side chain thereof or a neutral amino acid residue whose side chain may be substituted, preferably L-serine, L-threonine, L-asparagine or the like, $A^{11}$ is glycine, $A^{12}$ is L-proline, $A^{13}$ is glycine, and $A^{14}$ is L-alanine or L-proline, $A^{15}$ is an L-amino acid residue having an aromatic side chain, preferably L-tryptophan or the like, $A^{16}$ is a neutral L-amino acid residue having a carbamoyl group, preferably L-glutamine or the like, $A^{17}$ is a neutral amino acid residue, preferably glycine or the like, $B^1$ is a neutral L-amino acid residue whose side chain may be substituted, preferably optionally substituted glycine, more preferably glycine or the like, $B^2$ and $B^4$ are the same or different, and represent a basic L-amino acid residue whose side chain may be substituted, and preferably $B^2$ is L-arginine, $B^3$ is L-arginine, and $B^4$ is L-lysine, $B^5$ is an L-amino acid residue having an aromatic side chain, preferably L-phenylalanine or the like, $B^6$ and $B^7$ are the same or different, and represent a basic L-amino acid residue whose side chain may be substituted, preferably L-arginine or the like, and $B^8$ is glutamine whose side chain may be substituted, preferably L-glutamine, L-pyroglutamic acid or the like.

Preferable examples of P1, Q1 and R1 include:

(1) hydrogen atom, (2) Arg-Gln, (3) Arg, (4) Gln, (5) pGlu, or (6) Arg-Arg-Gln or the like.

P1 is more preferably a hydrogen atom, pGlu or Arg-Arg-Gln, Q1 is more preferably a hydrogen atom, pGlu or Arg-Arg-Gln, and R1 is more preferably a hydrogen atom, pGlu or Arg-Arg-Gln (still more preferably a hydrogen atom or Arg-Arg-Gln).

In this specification, P2 represents a neutral amino acid residue whose side chain may be substituted or a basic amino acid residue whose side chain may be substituted, preferably L-alanine which may be substituted (in a side chain thereof), L-histidine which may be substituted (in a side chain thereof), etc.

In this specification, P3 and Q2 represent a neutral amino acid residue whose side chain may be substituted, an aromatic amino acid residue whose side chain may be substituted, or a basic amino acid residue whose side chain may be substituted. The substituent group on a side chain of the basic amino acid residue includes, for example, a $C_{1-4}$ acyl group, a tosyl group, a $C_{1-6}$ alkyl group etc.

The $C_{1-4}$ acyl group includes, for example, a $C_{1-4}$ acyl group such as formyl, acetyl, propionyl and butyryl and $C_{2-4}$ alkanoyl group.

The $C_{1-6}$ alkyl group includes, for example, methyl, ethyl, propyl, isopropyl, butyl, isobutyl, sec-butyl, tert-butyl, pentyl, hexyl etc.

P3 and Q2 are preferably L-lysine whose side chain may be substituted, L-norleucine whose side chain may be substituted or L-arginine whose side chain may be substituted, more preferably L-lysine, L-norleucine or L-arginine whose side chain may be substituted with a $C_{1-4}$ acyl group (e.g., formyl, acetyl, propionyl, butyryl and $C_{2-4}$ alkanoyl), a $C_{1-6}$ alkyl group (e.g., methyl, ethyl, propyl, isopropyl, butyl, isobutyl, sec-butyl, tert-butyl, pentyl, hexyl etc.). or a tosyl group, more preferably L-lysine, L-norleucine, L-arginine, $N^ε$-acetyllysine, $N^ε$-methyllysine, $N^ε$-tosyllysine, $N^g$-tosylarginine etc.

Preferably, P3 and Q2 are optionally substituted L-arginine or optionally substituted L-lysine.

In this specification, P4 and Q3 represent a bond, a neutral amino acid whose side chain may be substituted or an aromatic amino acid residue whose side chain may be substituted. Each of P4 and Q3 is preferably a bond, L-norleucine whose side chain may be substituted, L-methionine whose side chain may be substituted, L-methionine sulfoxide whose side chain may be substituted or L-alanine whose side chain may be substituted, more preferably a bond, L-norleucine, L-methionine, L-methionine sulfoxide or L-cyclohexylalanine.

Further, P4 is particularly preferably L-norleucine, L-methionine or L-cyclohexylalanine. Q3 is particularly preferably a bond, L-methionine or L-cyclohexylalanine.

In this specification, P5 and Q4 represent [1] an amino acid residue whose side chain may be substituted, or its amino acid derivative wherein the C-terminal carboxyl group has been reduced to a hydroxymethyl group or formyl group, [2] a hydroxyl group, or [3] a dipeptide chain formed by binding an amino acid residue whose side chain may be substituted, to an amino acid residue whose side chain may be substituted, or its peptide derivative wherein the C-terminal carboxyl group has been reduced to a hydroxymethyl group or formyl group.

Each of P5 and Q4 is preferably [1] an amino acid residue whose side chain may be substituted, or its amino acid derivative wherein the C-terminal carboxyl group has been reduced to a hydroxymethyl group or formyl group, [2] a hydroxyl group or [3] a dipeptide chain formed by binding a neutral amino acid residue whose side chain may be substituted, to an amino acid residue having an aromatic side group which may be substituted, or its peptide derivative wherein the C-terminal carboxyl group has been reduced to a hydroxymethyl group or formyl group.

Each of P5 and Q4 is more preferably [1] L-proline whose side chain may be substituted, or its amino acid derivative wherein the C-terminal carboxyl group has been reduced to a hydroxymethyl group or formyl group, [2] 4-chlorophenylalanine whose side chain may be substituted, or its amino acid derivative wherein the C-terminal carboxyl group has been reduced to a hydroxymethyl group or formyl group, [3] 2-naphthylalanine whose side chain may be substituted, or its amino acid derivative wherein the C-terminal carboxyl group has been reduced to a hydroxymethyl group or formyl group, [4] cyclohexylalanine whose side chain may be substituted, or its amino acid derivative wherein the C-terminal carboxyl group has been reduced to a hydroxymethyl group or formyl group, [5] a hydroxyl group, or [6] a dipeptide chain formed by binding optionally substituted L-proline to (a) L-phenylalanine whose side chain may be substituted, (b) L-tyrosine whose side chain may be substituted, (c) L-2-thienylalanine whose side chain may be substituted, (d) L-phenylglycine whose side chain may be substituted or (e) L-2-pyridylalanine whose side chain may be substituted, or its peptide derivative wherein the C-terminal carboxyl group has been reduced to a hydroxymethyl group or formyl group.

Each of P5 and Q4 is still more preferably (1) L-proline or its amino acid derivative wherein the C-terminal carboxyl group has been reduced to a hydroxymethyl group or formyl group, (2) 4-chlorophenylalanine or its amino acid derivative wherein the C-terminal carboxyl group has been reduced to a hydroxymethyl group or formyl group, (3) 2-naphthylalanine or its amino acid derivative wherein the C-terminal carboxyl group has been reduced to a hydroxymethyl group or formyl group, (4) cyclohexylalanine or its amino acid derivative wherein the C-terminal carboxyl group has been reduced to a hydroxymethyl group or formyl group, (5) a hydroxyl group, (6) a dipeptide chain formed by binding L-proline to L-phenylalanine, or its peptide derivative wherein the C-terminal carboxyl group of the dipeptide has been reduced to a hydroxymethyl group or formyl group, (7) a dipeptide chain formed by binding L-proline to L-tyrosine, or its peptide derivative wherein the C-terminal carboxyl group has been reduced to a hydroxymethyl group or formyl group, (8) a dipeptide chain formed by binding L-proline to L-2-thienylalanine, or its peptide derivative wherein the C-terminal carboxyl group of the dipeptide has been reduced to a hydroxymethyl group or formyl group, (9) a dipeptide chain formed by binding L-proline to L-phenylglycine, or its peptide derivative wherein the C-terminal carboxyl group has been reduced to a hydroxymethyl group or formyl group, (10) a dipeptide chain formed by binding L-proline to 4-chlorophenylalanine, or its peptide derivative wherein the C-terminal carboxyl group has been reduced to a hydroxymethyl group or formyl group, (11) a dipeptide chain formed by binding L-proline to 2-naphthylalanine, or its peptide derivative wherein the C-terminal carboxyl group has been reduced to a hydroxymethyl group or formyl group, (12) a dipeptide chain formed by binding L-proline to 3-iodotyrosine, or its peptide derivative wherein the C-terminal carboxyl group has been reduced to a hydroxymethyl group or formyl group, (13) a dipeptide chain formed by binding L-proline to o-methyltyrosine, or its peptide derivative wherein the C-terminal carboxyl group has been reduced to a hydroxymethyl group or formyl group, or (14) a dipeptide chain formed by binding L-proline to L-2-pyridylalanine, or its peptide derivative wherein the C-terminal carboxyl group has been reduced to a hydroxymethyl group or formyl group.

Particularly preferable examples of "-P4-P5" and "-Q3-Q4" include:

(1) -Nle-Pro-Phe, (2) -Nle-Pro-Tyr, (3) -Nle-Pro, (4) -Nle, (5) -Met-Pro-Phe, (6) -Nle-Pro-Thi, (7) -Nle-Pro-Phg, (8) -Nle-Pro-Pya(2), (9) -Met(O),

(10) -Met-Phe(Cl),

(11) -Met-Pro-Phe(Cl),

(12) -Met-Pro-Nal(2),

(13) -Met-Nal(2),

(14) -Met-Cha,

(15) -Cha-Pro-Phe,

(16) -Cha,

(17) -Met-Pro-Tyr(I),

(18) -Cha-Pro-Phe(Cl),

(19) -Cha-Phe(Cl),

(20) -Nle-Pro-Tyr(I),

(21) -Nle-Phe(Cl),

(22) -Cha-Pro-Tyr(I),

(23) -Cha-Tyr(I),

(24) -Cha-Phe,

(25) -Met-Phe,

(26) -Met-Pro-Tyr(Me),

(27) —OH,

(28) -Met,

(29) -Met-Pro-Phe, and

(30) -Ala-Pro-Phe(Cl) or the like.

Still more preferable examples of "-P4-P5" include:

(1) -Cha-Pro-Phe(Cl), (2) -Cha-Pro-Phe, (3) -Met-Pro-Phe(Cl), (4) -Met-Pro-Phe (5) -Cha-Phe, and (6) -Met-Phe, more preferably (1) -Cha-Pro-Phe(Cl), (2) -Cha-Pro-Phe, (3) -Met-Pro-Phe(Cl), and (4) -Met-Pro-Phe.

Still more preferable examples of "-Q3-Q4" include:

(1) -Met-Pro-Phe(Cl), (2) -Cha-Phe(Cl), (3) -Cha-Pro-Phe(Cl), (4) -Cha, (5) -Cha-Pro-Phe, (6) —OH, (7) -Met, (8) -Met-Pro-Phe, and (9) -Ala-Pro-Phe(Cl).

In this specification, Q5 represents a neutral amino acid residue whose side chain may be substituted, preferably optionally substituted L-proline, optionally substituted L-glycine or optionally substituted L-alanine.

Q5 is particularly preferably L-proline, L-glycine or L-alanine.

In this specification, R2 represents optionally substituted L-cyclohexylalanine, preferably L-cyclohexylalanine.

In this specification, R3 represents optionally substituted L-phenylalanine, optionally substituted L-2-naphthylalanine, optionally substituted L-cyclohexylalanine or optionally substituted tyrosine, preferably L-4-chlorophenylalanine, L-2-naphthylalanine, L-cyclohexylalanine, L-phenylalanine or L-tyrosine.

The peptides of the present invention include, for example:

(1) Arg-Arg-Gln-Arg-Pro-Arg-Leu-Ser-Ala-Arg-Gly-Pro-Met-Pro-Phe(Cl) (SEQ ID NO: 1), (2) Arg-Arg-Gln-Arg-Pro-Arg-Leu-Ser-His-Lys-Gly-Pro-Cha-Pro-Phe(Cl) (SEQ ID NO: 2), (3) Arg-Pro-Arg-Leu-Ser-Ala-Arg-Gly-Pro-Met-Pro-Phe(Cl) (SEQ ID NO: 3), (4) Arg-Pro-Arg-Leu-Ser-Ala-Arg-Gly-Pro-Cha-Phe(Cl) (SEQ ID NO: 4), (5) Arg-Pro-Arg-Leu-Ser-Ala-Arg-Gly-Pro-Cha-Pro-Phe(Cl) (SEQ ID NO: 5), (6) Arg-Arg-Gln-Arg-Pro-Arg-Leu-Ser-Ala-Arg-Gly-Pro-Cha (SEQ ID NO: 6), (7) Arg-Pro-Arg-Leu-Ser-His-Lys-Gly-Pro-Cha-Pro-Phe(Cl) (SEQ ID NO: 7), (8) Arg-Pro-Arg-Leu-Ser-His-Lys-Gly-Pro-Met-Pro-Phe(Cl) (SEQ ID NO: 8), (9) pGlu-Arg-Pro-Arg-Leu-Ser-His-Lys-Gly-Pro-Cha-Pro-Phe (SEQ ID NO: 9),

(10) pGlu-Arg-Pro-Arg-Leu-Ser-His-Lys-Gly-Pro-Met-Pro-Phe(Cl) (SEQ ID NO: 10),

(11) Arg-Pro-Arg-Leu-Ser-Ala-Arg-Gly-Pro-Cha-Pro-Phe (SEQ ID NO: 11),

(12) Arg-Pro-Arg-Leu-Phe-Ala-Arg-Gly-Pro-Cha-Pro-Phe(Cl) (SEQ ID NO: 12),

(13) Arg-Pro-Arg-Leu-Phe-His-Lys-Gly-Pro-Cha-Pro-Phe(Cl) (SEQ ID NO: 13),

(14) Arg-Arg-Gln-Arg-Pro-Arg-Leu-Ser-His-Lys-Gly-Pro-Nle-Pro-Tyr (SEQ ID NO: 14),

(15) Arg-Pro-Arg-Leu-Phe-His-Lys-Gly-Pro-Cha-Pro-Phe (SEQ ID NO: 15),

(16) Arg-Pro-Arg-Leu-Phe-His-Lys-Gly-Pro-Met-Pro-Phe(Cl) (SEQ ID NO: 16),

(17) Arg-Arg-Gln-Arg-Pro-Arg-Leu-Ser-Ala-Arg-Gly-Pro-Met-Pro-Phe (SEQ ID NO: 21),

(18) Arg-Arg-Gln-Arg-Pro-Arg-Leu-Ser-Ala-Arg-Gly-Pro-Met (SEQ ID NO: 22),

(19) Arg-Arg-Gln-Arg-Pro-Arg-Leu-Ser-Ala-Arg-Gly-Pro (SEQ ID NO: 23),

(20) Arg-Arg-Gln-Arg-Pro-Arg-Leu-Ser-His-Lys-Gly-Pro-Met(O) (SEQ ID NO: 24),

(21) Arg-Arg-Lys(Arg-Arg)-Arg-Pro-Arg-Leu-Ser-His-Lys-Gly-Pro-Met-Pro-Phe (SEQ ID NO: 25),

(22) Arg-Arg-Arg-Arg-Pro-Arg-Leu-Ser-His-Lys-Gly-Pro-Met-Pro-Phe (SEQ ID NO: 26),

(23) Arg-Arg-Lys-Arg-Pro-Arg-Leu-Ser-His-Lys-Gly-Pro-Met-Pro-Phe (SEQ ID NO: 27),

(24) Arg-Pro-Arg-Leu-Ser-Ala-Arg-Gly-Pro-Met-Pro-Phe (SEQ ID NO: 28),

(25) Arg-Arg-Ala-Arg-Pro-Arg-Leu-Ser-His-Lys-Gly-Pro-Met-Pro-Phe (SEQ ID NO: 29),

(26) pGlu-Arg-Pro-Arg-Leu-Ser-Ala-Arg-Gly-Pro-Met-Pro-Phe (SEQ ID NO: 30),

(27) Arg-Pro-Arg-Leu-Ser-Ala-Arg-Gly-Pro-Met (SEQ ID NO: 31),

(28) Arg-Pro-Arg-Leu-Ser-His-Lys-Gly-Pro-Met-Phe(Cl) (SEQ ID NO: 32),

(29) pGlu-Arg-Pro-Arg-Leu-Ser-Ala-Lys-Gly-Pro-Met-Pro-Phe (SEQ ID NO: 33),

(30) pGlu-Arg-Pro-Arg-Leu-Ser-Arg-Lys-Gly-Pro-Met-Pro-Phe (SEQ ID NO: 34),

(31) Arg-Pro-Arg-Leu-Phe-Ala-Arg-Gly-Pro-Met-Pro-Phe (SEQ ID NO: 35),

(32) Arg-Pro-Arg-Leu-Ser-His-Lys-Gly-Pro-Met-Pro-Nal (2) (SEQ ID NO: 36),

(33) Arg-Arg-Phe-Arg-Pro-Arg-Leu-Ser-His-Lys-Gly-Pro-Met-Pro-Phe (SEQ ID NO: 37),

(34) pGlu-Arg-Pro-Arg-Leu-Ser-His-Arg-Gly-Pro-Met-Pro-Phe (SEQ ID NO: 38),

(35) pGlu-Arg-Pro-Arg-Leu-Ser-His-Lys-Gly-Pro-Met-Phe(Cl) (SEQ ID NO: 39),

(36) Arg-Pro-Arg-Leu-Ser-His-Lys-Gly-Pro-Met-Cha (SEQ ID NO: 40),

(37) Arg-Pro-Arg-Leu-Phe-His-Lys-Gly-Pro-Cha-Phe(Cl) (SEQ ID NO: 41),

(38) pGlu-Arg-Pro-Arg-Leu-Ser-Leu-Lys-Gly-Pro-Met-Pro-Phe (SEQ ID NO: 42),

(39) pGlu-Arg-Pro-Arg-Leu-Ser-His-Lys-Gly-Pro-Met-Pro-Nal (2) (SEQ ID NO: 43),

(40) Arg-Pro-Arg-Leu-Ser-His-Lys-Gly-Pro-Met-Nal (2) (SEQ ID NO: 44),

(41) pGlu-Arg-Pro-Arg-Leu-Ser-Arg-Arg-Gly-Pro-Met-Pro-Phe (SEQ ID NO: 45),

(42) pGlu-Arg-Pro-Arg-Leu-Phe-Arg-Arg-Gly-Pro-Met-Pro-Phe (SEQ ID NO: 46),

(43) pGlu-Arg-Pro-Arg-Leu-Ser-Phe-Lys-Gly-Pro-Met-Pro-Phe (SEQ ID NO: 47),

(44) pGlu-Arg-Pro-Arg-Leu-Phe-His-Lys-Gly-Pro-Met-Pro-Phe (SEQ ID NO: 48),

(45) pGlu-Arg-Pro-Arg-Leu-Ser-His-Lys-Gly-Pro-Met-Cha (SEQ ID NO: 49),

(46) pGlu-Arg-Pro-Arg-Leu-Ser-His-Lys-Gly-Pro-Met-Nal (2) (SEQ ID NO: 50),

(47) Arg-Pro-Arg-Leu-Phe-Ala-Arg-Gly-Pro-Met-Phe (SEQ ID NO: 51),

(48) pGlu-Arg-Pro-Arg-Leu-Ser-His-Phe-Gly-Pro-Met-Pro-Phe (SEQ ID NO: 52),

(49) Arg-Pro-Arg-Leu-Ser-His-Lys-Gly-Pro-Met-Pro-Cha (SEQ ID NO: 53),

(50) pGlu-Arg-Pro-Arg-Leu-Ser-His-Leu-Gly-Pro-Met-Pro-Phe (SEQ ID NO: 54),

(51) Arg-Arg-Gln-Arg-Pro-Arg-Leu-Ser-Ala-Arg-Gly-NMe$_2$ (SEQ ID NO: 55),

(52) Arg-Arg-Gln-Arg-Pro-Arg-Leu-Ser-Ala-Arg-Gly-Mor (SEQ ID NO: 56),

(53) Arg-Pro-Arg-Leu-Ser-Ala-Arg-Gly-Pro-Ala-Pro-Phe (Cl) (SEQ ID NO: 57),

(54) Arg-Pro-Arg-Leu-Ser-Ala-Arg-Gly-Gly-Met-Pro-Phe (Cl) (SEQ ID NO: 58),

(55) Arg-Pro-Arg-Leu-Ser-Ala-Arg-Gly-N-MeAla-Met-Pro-Phe(Cl) (SEQ ID NO: 59),

(56) Arg-Pro-Arg-Leu-Ser-His-Ala-Gly-Pro-Cha-Pro-Phe (Cl) (SEQ ID NO: 60),

(57) Arg-Pro-Arg-Ala-Ser-His-Lys-Gly-Pro-Cha-Pro-Phe (Cl) (SEQ ID NO: 61),

(58) Arg-Pro-Ala-Leu-Ser-His-Lys-Gly-Pro-Cha-Pro-Phe (Cl) (SEQ ID NO: 62),

(59) Arg-Arg-Gln-Arg-Pro-Arg-Leu-Ser-Ala-Arg-Gly-Pro-Met-Pro-Phe(Cl)—NH$_2$ (SEQ ID NO: 63),

(60) Arg-Pro-Arg-Leu-Ser-Ala-Arg-Gly-Pro-Cha-Pyn (SEQ ID NO: 64),

(61) Arg-Pro-Arg-Leu-Ser-Ala-Arg-Gly-Pro-Cha-Pro-Pyn (SEQ ID NO: 65),

(62) Arg-Arg-Gln-Arg-Pro-Arg-Leu-Ser-Ala-Arg-Gly-Gly-Cha (SEQ ID NO: 66),

(63) Arg-Pro-Lys(Me)$_2$-Leu-Ser-Ala-Arg-Gly-Pro-Met-Pro-Phe (SEQ ID NO: 67),

(64) Arg-Pro-Arg-Leu-Ser-Ala-Lys(Me)$_2$-Gly-Pro-Met-Pro-Phe (SEQ ID NO: 68),

(65) Arg-Pro-Arg-Leu-Ser-Dap-Arg-Gly-Pro-Cha-Pro-Phe (Cl) (SEQ ID NO: 69),

(66) Arg-Pro-Arg-Leu-Ser-Dap(Ac)-Arg-Gly-Pro-Cha-Pro-Phe(Cl) (SEQ ID NO: 70),

(67) Arg-Pro-Arg-Leu-Ser-Dap(C$_6$)-Arg-Gly-Pro-Cha-Pro-Phe(Cl) (SEQ ID NO: 71), and

(68) Arg-Pro-Arg-Leu-Ser-Dap(Adi)-Arg-Gly-Pro-Cha-Pro-Phe(Cl) (SEQ ID NO: 72).

The peptide represented by the above formula P1-Arg-Pro-Arg-Leu-Phe-P2-P3-Gly-Pro-P4-P5 (I) (SEQ ID NO: 73), or esters thereof or salts thereof, include peptides represented by:

[1] Arg-Pro-Arg-Leu-Phe-Ala-Arg-Gly-Pro-Cha-Pro-Phe (Cl) (SEQ ID NO: 12),

[2] Arg-Pro-Arg-Leu-Phe-His-Lys-Gly-Pro-Cha-Pro-Phe (Cl) (SEQ ID NO: 13),

[3] Arg-Pro-Arg-Leu-Phe-His-Lys-Gly-Pro-Cha-Pro-Phe (SEQ ID NO: 15),

[4] Arg-Pro-Arg-Leu-Phe-His-Lys-Gly-Pro-Met-Pro-Phe (Cl) (SEQ ID NO: 16),

[5] Arg-Pro-Arg-Leu-Phe-Ala-Arg-Gly-Pro-Met-Pro-Phe (SEQ ID NO: 35),

[6] Arg-Pro-Arg-Leu-Phe-His-Lys-Gly-Pro-Cha-Phe(Cl) (SEQ ID NO: 41),

[7] pGlu-Arg-Pro-Arg-Leu-Phe-Arg-Arg-Gly-Pro-Met-Pro-Phe (SEQ ID NO: 46),

[8] pGlu-Arg-Pro-Arg-Leu-Phe-His-Lys-Gly-Pro-Met-Pro-Phe (SEQ ID NO: 48),

[9] Arg-Pro-Arg-Leu-Phe-Ala-Arg-Gly-Pro-Met- Phe (SEQ ID NO: 51)

or esters thereof or salts thereof.

The peptide represented by the above formula Q1-Arg-Pro-Arg-Leu-Ser-Ala-Q2-Gly-Q5-Q3-Q4 (II) (SEQ ID NO: 75), or esters thereof or salts thereof, include peptides represented by:

(i) Arg-Arg-Gln-Arg-Pro-Arg-Leu-Ser-Ala-Arg-Gly-Pro-Met-Pro-Phe(Cl) (SEQ ID NO: 1), (ii) Arg-Pro-Arg-Leu-Ser-Ala-Arg-Gly-Pro-Met-Pro-Phe (Cl) (SEQ ID NO: 3), (iii) Arg-Pro-Arg-Leu-Ser-Ala-Arg-Gly-Pro-Cha-Phe(Cl) (SEQ ID NO: 4), (iv) Arg-Pro-Arg-Leu-Ser-Ala-Arg-Gly-Pro-Cha-Pro-Phe (Cl) (SEQ ID NO: 5), (v) Arg-Arg-Gln-Arg-Pro-Arg-Leu-Ser-Ala-Arg-Gly-Pro-Cha (SEQ ID NO: 6), (vi) Arg-Pro-Arg-Leu-Ser-Ala-Arg-Gly-Pro-Cha-Pro-Phe (SEQ ID NO: 11), (vii) Arg-Arg-Gln-Arg-Pro-Arg-Leu-Ser-Ala-Arg-Gly-Pro-Met-Pro-Phe (SEQ ID NO: 21), (viii) Arg-Arg-Gln-Arg-Pro-Arg-Leu-Ser-Ala-Arg-Gly-Pro-Met (SEQ ID NO: 22), (ix) Arg-Arg-Gln-Arg-Pro-Arg-Leu-Ser-Ala-Arg-Gly-Pro (SEQ ID NO: 23), (x) Arg-Pro-Arg-Leu-Ser-Ala-Arg-Gly-Pro-Met-Pro-Phe (SEQ ID NO: 28), (xi) pGlu-Arg-Pro-Arg-Leu-Ser-Ala-Arg-Gly-Pro-Met-Pro-Phe (SEQ ID NO: 30), (xii) Arg-Pro-Arg-Leu-Ser-Ala-Arg-Gly-Pro-Met (SEQ ID NO: 31), (xiii) pGlu-Arg-Pro-Arg-Leu-Ser-Ala-Lys-Gly-Pro-Met-Pro-Phe (SEQ ID NO: 33), (xiv) Arg-Pro-Arg-Leu-Ser-Ala-Arg-Gly-Pro-Ala-Pro-Phe (Cl) (SEQ ID NO: 57), (xv) Arg-Pro-Arg-Leu-Ser-Ala-Arg-Gly-Gly-Met-Pro-Phe (Cl) (SEQ ID NO: 58), (xvi) Arg-Pro-Arg-Leu-Ser-Ala-Arg-Gly-NMe-Ala-Met-Pro-Phe(Cl) (SEQ ID NO: 59), (xvii) Arg-Pro-Arg-Leu-Ser-Ala-Arg-Gly-Pro-Cha-Pyn (SEQ ID NO: 64), (xviii) Arg-Pro-Arg-Leu-Ser-Ala-Arg-Gly-Pro-Cha-Pro-Pyn (SEQ ID NO: 65), (xix) Arg-Arg-Gln-Arg-Pro-Arg-Leu-Ser-Ala-Arg-Gly-Gly-Cha (SEQ ID NO: 66), or (xx) Arg-Pro-Arg-Leu-Ser-Ala-Lys(Me)$_2$-Gly-Pro-Met-Pro-Phe (SEQ ID NO: 68), or esters thereof or salts thereof.

The peptide represented by the above formula R1-Arg-Pro-Arg-Leu-Ser-His-Lys-Gly-Pro-R2-Pro-R3 (III) (SEQ ID NO: 77), or esters thereof or salts thereof, include peptides represented by:

[1] Arg-Arg-Gln-Arg-Pro-Arg-Leu-Ser-His-Lys-Gly-Pro-Cha-Pro-Phe(Cl) (SEQ ID NO: 2),

[2] Arg-Pro-Arg-Leu-Ser-His-Lys-Gly-Pro-Cha-Pro-Phe (Cl) (SEQ ID NO: 7),

[3] Arg-Pro-Arg-Leu-Ser-His-Lys-Gly-Pro-Met-Pro-Phe (Cl) (SEQ ID NO: 8),

[4] pGlu-Arg-Pro-Arg-Leu-Ser-His-Lys-Gly-Pro-Cha-Pro-Phe (SEQ ID NO: 9),

[5] pGlu-Arg-Pro-Arg-Leu-Ser-His-Lys-Gly-Pro-Met-Pro-Phe(Cl) (SEQ ID NO: 10),

[6] Arg-Arg-Gln-Arg-Pro-Arg-Leu-Ser-His-Lys-Gly-Pro-Nle-Pro-Tyr (SEQ ID NO: 14),

[7] Arg-Pro-Arg-Leu-Ser-His-Lys-Gly-Pro-Met-Pro-Nal(2) (SEQ ID NO: 36),

[8] pGlu-Arg-Pro-Arg-Leu-Ser-His-Lys-Gly-Pro-Met-Pro-Nal(2) (SEQ ID NO: 43),

[9] Arg-Pro-Arg-Leu-Ser-His-Lys-Gly-Pro-Met-Pro-Cha (SEQ ID NO: 53)

or esters thereof or salts thereof.

Further, the present invention relates to peptides represented by:

(i) Arg-Arg-Gln-Arg-Pro-Arg-Leu-Ser-His-Lys-Gly-Pro-Met(O) (SEQ ID NO: 24), (ii) Arg-Arg-Lys(Arg-Arg)-Arg-Pro-Arg-Leu-Ser-His-Lys-Gly-Pro-Met-Pro-Phe (SEQ ID NO: 25), (iii) Arg-Arg-Arg-Arg-Pro-Arg-Leu-Ser-His-Lys-Gly-Pro-Met-Pro-Phe (SEQ ID NO: 26), (iv) Arg-Arg-Lys-Arg-Pro-Arg-Leu-Ser-His-Lys-Gly-Pro-Met-Pro-Phe (SEQ ID NO: 27), (v) Arg-Arg-Ala-Arg-Pro-Arg-Leu-Ser-His-Lys-Gly-Pro-Met-Pro-Phe (SEQ ID NO: 29), (vi) Arg-Pro-Arg-Leu-Ser-His-Lys-Gly-Pro-Met-Phe(Cl) (SEQ ID NO: 32), (vii) pGlu-Arg-Pro-Arg-Leu-Ser-Arg-Lys-Gly-Pro-Met-Pro-Phe (SEQ ID NO: 34), (viii) Arg-Arg-Phe-Arg-Pro-Arg-Leu-Ser-His-Lys-Gly-Pro-Met-Pro-Phe (SEQ ID NO: 37), (ix) pGlu-Arg-Pro-Arg-Leu-Ser-His-Arg-Gly-Pro-Met-Pro-Phe (SEQ ID NO: 38), (x) pGlu-Arg-Pro-Arg-Leu-Ser-His-Lys-Gly-Pro-Met-Phe (Cl) (SEQ ID NO: 39), (xi) Arg-Pro-Arg-Leu-Ser-His-Lys-Gly-Pro-Met-Cha (SEQ ID NO: 40), (xii) pGlu-Arg-Pro-Arg-Leu-Ser-Leu-Lys-Gly-Pro-Met-Pro-Phe (SEQ ID NO: 42), (xiii) Arg-Pro-Arg-Leu-Ser-His-Lys-Gly-Pro-Met-Nal(2) (SEQ ID NO: 44), (xiv) pGlu-Arg-Pro-Arg-Leu-Ser-Arg-Arg-Gly-Pro-Met-Pro-Phe (SEQ ID NO: 45), (xv) pGlu-Arg-Pro-Arg-Leu-Ser-Phe-Lys-Gly-Pro-Met-Pro-Phe (SEQ ID NO: 47), (xvi) pGlu-Arg-Pro-Arg-Leu-Ser-His-Lys-Gly-Pro-Met-Cha (SEQ ID NO: 49), (xvii) pGlu-Arg-Pro-Arg-Leu-Ser-His-Lys-Gly-Pro-Met-Nal(2) (SEQ ID NO: 50), (xviii) pGlu-Arg-Pro-Arg-Leu-Ser-His-Phe-Gly-Pro-Met-Pro-Phe (SEQ ID NO: 52), (xix) pGlu-Arg-Pro-Arg-Leu-Ser-His-Leu-Gly-Pro-Met-Pro-Phe (SEQ ID NO: 54), (xx) Arg-Arg-Gln-Arg-Pro-Arg-Leu-Ser-Ala-Arg-Gly-NMe2 (SEQ ID NO: 55), (xxi) Arg-Arg-Gln-Arg-Pro-Arg-Leu-Ser-Ala-Arg-Gly-Mor (SEQ ID NO: 56), (xxii) Arg-Pro-Arg-Leu-Ser-His-Ala-Gly-Pro-Cha-Pro-Phe (Cl) (SEQ ID NO: 60), (xxiii) Arg-Pro-Arg-Ala-Ser-His-Lys-Gly-Pro-Cha-Pro-Phe (Cl) (SEQ ID NO: 61), (xxiv) Arg-Pro-Lys(Me)$_2$-Leu-Ser-Ala-Arg-Gly-Pro-Met-Pro-Phe (SEQ ID NO: 67), (xxv) Arg-Pro-Arg-Leu-Ser-Dap-Arg-Gly-Pro-Cha-Pro-Phe (Cl) (SEQ ID NO: 69), (xxvi) Arg-Pro-Arg-Leu-Ser-Dap(Ac)-Arg-Gly-Pro-Cha-Pro-Phe(Cl) (SEQ ID NO: 70), (xxvii) Arg-Pro-Arg-Leu-Ser-Dap(C6)-Arg-Gly-Pro-Cha-Pro-Phe(Cl) (SEQ ID NO: 71), (xxviii) Arg-Pro-Arg-Leu-Ser-Dap(Adi)-Arg-Gly-Pro-Cha-Pro-Phe(Cl) (SEQ ID NO: 72), or (xxix) Arg-Pro-Ala-Leu-Ser-His-Lys-Gly-Pro-Cha-Pro-Phe (Cl) (SEQ ID NO: 62), or esters thereof or salts thereof.

Further, the present invention relates to peptides represented by:

(i) Arg-Arg-Gln-Arg-Pro-Arg-Leu-Ser-His-Lys-Gly-Pro-Met(O) (SEQ ID NO: 24), (ii) Arg-Arg-Lys(Arg-Arg)-Arg-Pro-Arg-Leu-Ser-His-Lys-Gly-Pro-Met-Pro-Phe (SEQ ID NO: 25), (iii) Arg-Arg-Arg-Arg-Pro-Arg-Leu-Ser-His-Lys-Gly-Pro-Met-Pro-Phe (SEQ ID NO: 26), (iv) Arg-Arg-Lys-Arg-Pro-Arg-Leu-Ser-His-Lys-Gly-Pro-Met-Pro-Phe (SEQ ID NO: 27), (v) Arg-Arg-Ala-Arg-Pro-Arg-Leu-Ser-His-Lys-Gly-Pro-Met-Pro-Phe (SEQ ID NO: 29), (vi) Arg-Pro-Arg-Leu-Ser-His-Lys-Gly-Pro-Met-Phe(Cl) (SEQ ID NO: 32), (vii) pGlu-Arg-Pro-Arg-Leu-Ser-Arg-Lys-Gly-Pro-Met-Pro-Phe (SEQ ID NO: 34), (viii) Arg-Arg-Phe-Arg-Pro-Arg-Leu-Ser-His-Lys-Gly-Pro-Met-Pro-Phe (SEQ ID NO: 37), (ix) pGlu-Arg-Pro-Arg-Leu-Ser-His-Arg-Gly-Pro-Met-Pro-Phe (SEQ ID NO: 38), (x) pGlu-Arg-Pro-Arg-Leu-Ser-His-Lys-Gly-Pro-Met-Phe (Cl) (SEQ ID NO: 39), (xi) Arg-Pro-Arg-Leu-Ser-His-Lys-Gly-Pro-Met-Cha (SEQ ID NO: 40), (xii) pGlu-Arg-Pro-Arg-Leu-Ser-Leu-Lys-Gly-Pro-Met-Pro-Phe (SEQ ID NO: 42), (xiii) Arg-Pro-Arg-Leu-Ser-His-Lys-Gly-Pro-Met-Nal(2) (SEQ ID NO: 44), (xiv) pGlu-Arg-Pro-Arg-Leu-Ser-Arg-Arg-Gly-Pro-Met-Pro-Phe (SEQ ID NO: 45), (xv) pGlu-Arg-Pro-Arg-Leu-Ser-Phe-Lys-Gly-Pro-Met-Pro-Phe (SEQ ID NO: 47), (xvi) pGlu-Arg-Pro-Arg-Leu-Ser-His-Lys-Gly-Pro-Met-Cha (SEQ ID NO: 49), (xvii) pGlu-Arg-Pro-Arg-Leu-Ser-His-Lys-Gly-Pro-Met-Nal(2) (SEQ ID NO: 50), (xviii) pGlu-Arg-Pro-Arg-Leu-Ser-His-Phe-Gly-Pro-Met-Pro-Phe (SEQ ID NO: 52), (xix) pGlu-Arg-Pro-Arg-Leu-Ser-His-Leu-Gly-Pro-Met-Pro-Phe (SEQ ID NO: 54), (xx) Arg-Arg-Gln-Arg-Pro-Arg-Leu-Ser-Ala-Arg-Gly-NMe2 (SEQ ID NO: 55), (xxi) Arg-Arg-Gln-Arg-Pro-Arg-Leu-Ser-Ala-Arg-Gly-Mor (SEQ ID NO: 56), (xxii) Arg-Pro-Arg-Leu-Ser-His-Ala-Gly-Pro-Cha-Pro-Phe (Cl) (SEQ ID NO: 60), (xxiii) Arg-Pro-Arg-Ala-Ser-His-Lys-Gly-Pro-Cha-Pro-Phe (Cl) (SEQ ID NO: 61), (xxiv) Arg-Pro-Lys(Me)$_2$-Leu-Ser-Ala-Arg-Gly-Pro-Met-Pro-Phe (SEQ ID NO: 67), (xxv) Arg-Pro-Arg-Leu-Ser-Dap-Arg-Gly-Pro-Cha-Pro-Phe (Cl) (SEQ ID NO: 69), (xxvi) Arg-Pro-Arg-Leu-Ser-Dap(Ac)c-Arg-Gly-Pro-Cha-Pro-Phe(Cl) (SEQ ID NO: 70), (xxvii) Arg-Pro-Arg-Leu-Ser-Dap(C6)-Arg-Gly-Pro-Cha-Pro-Phe(Cl) (SEQ ID NO: 71), (xxviii) Arg-Pro-Arg-Leu-Ser-Dap(Adi)-Arg-Gly-Pro-Cha-Pro-Phe(Cl) (SEQ ID NO: 72), or (xxix) Arg-Pro-Ala-Leu-Ser-His-Lys-Gly-Pro-Cha-Pro-Phe (Cl) (SEQ ID NO: 62), or esters thereof or salts thereof.

---

The invention claimed is:

1. A peptide represented by the formula:

P1-Arg-Pro-Arg-Leu-Phe-P2-P3-Gly-Pro-P4-P5 (I) (SEQ ID NO: 73)

wherein P1 represents a hydrogen atom, or an amino acid residue or a peptide chain, consisting of 1 to 25 amino acids which may be the same or different and whose side chain may be substituted, P2 represents a neutral amino acid residue whose side chain may be substituted or a basic amino acid residue whose side chain may be substituted, P3 represents a neutral amino acid residue whose side chain may be substituted, an aromatic amino acid residue whose side chain may be substituted or a basic amino acid residue whose side chain may be substituted, P4 represents a bond or a neutral or aromatic amino acid residue whose side chain may be substituted, P5 represents [1] an amino acid residue whose side chain may be substituted, or its amino acid derivative wherein the C-terminal carboxyl group has been reduced to a hydroxymethyl group or formyl group, [2] a hydroxyl group, or [3] a dipeptide chain formed by binding an amino acid residue whose side chain may be substituted, to an amino acid residue whose side chain may be substituted, or its peptide derivative wherein the C-terminal carboxyl group of the dipeptide has been reduced to a hydroxymethyl group or formyl group, and a side chain of each amino acid residue in the formula -Arg-Pro-Arg-Leu-Phe- (SEQ ID NO: 74) or -Gly-Pro- may be substituted; an ester thereof or an amide thereof, or a salt thereof.

2. The peptide according to claim 1, an ester thereof or an amide thereof, or a salt thereof, wherein P1 is a hydrogen atom, pGlu or Arg-Arg-Gln.

3. The peptide according to claim 1, an ester thereof or an amide thereof, or a salt thereof, wherein P2 is optionally substituted His or optionally substituted Ala.

4. The peptide according to claim 1, an ester thereof or an amide thereof, or a salt thereof, wherein P3 is optionally substituted Arg or optionally substituted Lys.

5. The peptide according to claim 1, an ester thereof or an amide thereof, or a salt thereof, wherein -P4-P5 is -Cha-Pro-Phe(Cl), -Cha-Pro-Phe, -Met-Pro-Phe, -Met-Pro-Phe(Cl), -Cha-Phe or -Met-Phe.

6. The peptide according to claim 1, which is represented by:

[1] Arg-Pro-Arg-Leu-Phe-Ala-Arg-Gly-Pro-Cha-Pro-Phe(Cl) (SEQ ID NO: 12),

[2] Arg-Pro-Arg-Leu-Phe-His-Lys-Gly-Pro-Cha-Pro-Phe(Cl) (SEQ ID NO: 13),

[3] Arg-Pro-Arg-Leu-Phe-His-Lys-Gly-Pro-Cha-Pro-Phe (SEQ ID NO: 15),

[4] Arg-Pro-Arg-Leu-Phe-His-Lys-Gly-Pro-Met-Pro-Phe(Cl) (SEQ ID NO: 16),

[5] Arg-Pro-Arg-Leu-Phe-Ala-Arg-Gly-Pro-Met-Pro-Phe (SEQ ID NO: 35),

[6] Arg-Pro-Arg-Leu-Phe-His-Lys-Gly-Pro-Cha-Phe(Cl) (SEQ ID NO: 41),

[7] pGlu-Arg-Pro-Arg-Leu-Phe-Arg-Arg-Gly-Pro-Met-Pro-Phe (SEQ ID NO: 46),

[8] pGlu-Arg-Pro-Arg-Leu-Phe-His-Lys-Gly-Pro-Met-Pro-Phe (SEQ ID NO: 48), or

[9] Arg-Pro-Arg-Leu-Phe-Ala-Arg-Gly-Pro-Met-Phe (SEQ ID NO: 51), an ester thereof or an amide thereof, or a salt thereof.

* * * * *